(12) United States Patent
Demmer

(10) Patent No.: US 9,468,772 B2
(45) Date of Patent: Oct. 18, 2016

(54) MULTI-DEVICE IMPLANTABLE MEDICAL DEVICE SYSTEM AND PROGRAMMING METHODS

(71) Applicant: Medtronic, Inc., Minneapolis, MN (US)

(72) Inventor: Wade M Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/601,915

(22) Filed: Jan. 21, 2015

(65) Prior Publication Data

US 2016/0206892 A1     Jul. 21, 2016

(51) Int. Cl.
| | |
|---|---|
| *A61N 1/00* | (2006.01) |
| *A61N 1/372* | (2006.01) |
| *A61N 1/368* | (2006.01) |
| *A61N 1/39* | (2006.01) |

(52) U.S. Cl.
CPC ........... *A61N 1/37288* (2013.01); *A61N 1/368* (2013.01); *A61N 1/37223* (2013.01); *A61N 1/37247* (2013.01); *A61N 1/3956* (2013.01)

(58) Field of Classification Search
CPC ..................... A61N 1/37288; A61N 1/36132; H04L 41/0809
See application file for complete search history.

(56) References Cited

U.S. PATENT DOCUMENTS

| | | |
|---|---|---|
| 4,494,950 A | 1/1985 | Fischell |
| 5,354,316 A | 10/1994 | Keimel |
| 5,456,692 A | 10/1995 | Smith, Jr. et al. |
| 5,507,782 A | 4/1996 | Kieval et al. |
| 5,545,186 A | 8/1996 | Olson et al. |
| 5,683,432 A | 11/1997 | Goedeke et al. |
| 5,725,559 A | 3/1998 | Alt et al. |
| 6,393,316 B1 | 5/2002 | Gillberg et al. |
| 6,442,433 B1 | 8/2002 | Linberg |
| 6,471,645 B1 | 10/2002 | Warkentin et al. |
| 6,599,250 B2 | 7/2003 | Webb et al. |
| 6,647,434 B1 | 11/2003 | Kamepalli |
| 7,031,771 B2 | 4/2006 | Brown et al. |
| 7,181,505 B2 | 2/2007 | Haller et al. |
| 7,565,197 B2 | 7/2009 | Haubrich et al. |
| 7,720,543 B2 | 5/2010 | Dudding et al. |
| 7,742,816 B2 | 6/2010 | Masoud et al. |
| 7,949,404 B2 | 5/2011 | Hill |
| 8,102,789 B2 | 1/2012 | Rosar et al. |
| 8,160,684 B2 | 4/2012 | Ghanem et al. |
| 8,352,025 B2 | 1/2013 | Jacobson |
| 8,352,038 B2 | 1/2013 | Mao et al. |
| 8,433,409 B2 | 4/2013 | Johnson et al. |
| 8,437,842 B2 | 5/2013 | Zhang et al. |
| 8,532,785 B1 | 9/2013 | Crutchfield et al. |

(Continued)

OTHER PUBLICATIONS (PCT/US2016/013139) PCT Notification of Transmittal of the International Search Report and the Written Opinion of the International Searching Authority, mailed Apr. 14, 2016, 12 pages.

*Primary Examiner* — Robert N Wieland
(74) *Attorney, Agent, or Firm* — Evans M. Mburu

(57) ABSTRACT

An external medical device is capable of bidirectional wireless communication with multiple implantable medical devices (IMDs). The external medical device is configured to determine an active membership of an IMD system present in a patient, establish programmable parameters for the IMD system based on the active membership, and transmit values for the established programmable parameters to the active membership.

33 Claims, 10 Drawing Sheets

(56) References Cited

U.S. PATENT DOCUMENTS

| | | |
|---|---|---|
| 8,542,131 B2 | 9/2013 | Jahn |
| 2002/0013613 A1 | 1/2002 | Haller et al. |
| 2006/0135999 A1 | 6/2006 | Bodner et al. |
| 2007/0299480 A1 | 12/2007 | Hill |
| 2009/0299438 A1 | 12/2009 | Nolan et al. |
| 2012/0016305 A1* | 1/2012 | Jollota ............... A61B 5/14532 604/151 |
| 2013/0035748 A1 | 2/2013 | Bonner et al. |
| 2014/0121719 A1 | 5/2014 | Bonner et al. |
| 2014/0214104 A1 | 7/2014 | Greenhut et al. |
| 2014/0337922 A1* | 11/2014 | Sievert ............... A61N 1/37282 726/3 |

* cited by examiner

| IF ACTIVE MEMBERSHIP = ⟋602 | PROVIDE PROGRAMMABLE PARAMETERS TO: ⟋604 |
|---|---|
| RA pacemaker | Enable: A brady single chamber pacing modes, AV conduction monitoring<br>Disable: Dual chamber pacing modes, A tachy detection and A ATP therapy |
| RV pacemaker | Enable: V brady single chamber pacing modes<br>Disable: Dual chamber pacing modes, VT detection and ATP therapy |
| LV pacemaker | Enable: CRT therapy<br>Disable: Dual chamber pacing modes, VT detection and V ATP therapy |
| RA pacemaker + RV pacemaker | Enable: A brady single chamber pacing modes, Dual chamber sensing in RA, V brady single chamber pacing modes, Dual chamber pacing modes, A tachy detection and A ATP therapy, minimum V pacing and AV conduction monitoring in RV pacemaker<br>Disable: VT detection and ATP therapy; AV conduction monitoring in RA pacemaker |
| RA pacemaker + RV pacemaker + LV pacemaker | .... |
| RA pacemaker + ICD | .... |
| RV pacemaker + ICD | .... |
| LV pacemaker + ICD | .... |
| Etc... | .... |

MULTI-DEVICE IMPLANTABLE MEDICAL DEVICE SYSTEM AND PROGRAMMING METHODS

TECHNICAL FIELD

The disclosure relates to an implantable medical device system that may include multiple devices implanted in a given patient and an external device for establishing and programming control parameters used by the implanted devices in the context of the other implantable device(s) that are present in the patient.

BACKGROUND

A variety of implantable medical devices (IMDs) for delivering a therapy, monitoring a physiological condition of a patient or a combination thereof have been clinically implanted or proposed for clinical implantation in patients. IMDs may deliver therapy to or monitor conditions of a variety of organs, nerves, muscle or tissue, such as the heart, brain, stomach, spinal cord, pelvic floor, or the like. The IMDs may employ stimulation electrodes, sense electrodes, and/or other sensors carried by one or more elongated electrical leads or within or along the housing of the IMD.

Some IMDs, such as cardiac pacemakers or implantable cardioverter defibrillators (ICDs), provide therapeutic electrical stimulation to or monitor the heart of the patient. The electrical stimulation provided by the IMD may include signals such as pacing pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal cardiac rhythms. Upon detection of an abnormal rhythm, the device may deliver an appropriate electrical stimulation signal or signals to restore or maintain a more normal rhythm. For example, an IMD may deliver pacing pulses to the heart upon detecting tachycardia or bradycardia or deliver cardioversion or defibrillation shocks to the heart upon detecting tachycardia or fibrillation.

More than one IMD may be implanted in a patient based on individual patient need. More than one IMD may be required for monitoring conditions that may require a therapy and for delivering different types of therapies. In some cases, more than one IMD may be required to monitor cardiac signals and deliver therapies to different chambers of the heart, or more generally monitor physiological signals and deliver therapy at various sites in the patient's body.

SUMMARY

In general, the disclosure is directed to an implantable medical device (IMD) system that includes an external programmer and multiple IMDs programmable by the external programmer. The programmer establishes programmable features of an active IMD system based on determining and identifying each IMD that is present and operable in the patient. The programmable features are established to enable programming of monitoring and/or therapy delivery functions of the separate IMDs present in the patient in a manner that yields coordinated IMD system operation when more than one IMD is implanted. The coordinated system operation of multiple IMDs enables maximum functionality of a particular combination of IMDs to promote optimal patient safety and benefit and may reduce redundant functions of the IMD system as a whole.

In one example, the disclosure provides an external device comprising a telemetry module configured for bidirectional wireless communication with a plurality of implantable medical devices and a control module configured to determine an active membership of an implantable medical device (IMD) system, wherein the active membership comprises each one of the plurality of implantable medical devices present in a patient, establish programmable parameters for the IMD system based on the active membership, and control the telemetry module to transmit values for the established programmable parameters to the active membership.

In another example, the disclosure provides a method comprising determining an active membership of an implantable medical device (IMD) system by a control module of an external device configured for bidirectional communication with a plurality of implantable medical devices, wherein the active membership comprises each one of the plurality of implantable medical devices that is present in a patient and operable; establishing programmable parameters for the IMD system based on the active membership; and transmitting values for the established programmable parameters to the active membership.

In another example, the disclosure provides an IMD system comprising: a plurality of implantable medical devices and an external device. The external device includes a control module and a telemetry module configured for bidirectional wireless communication with the plurality of implantable medical devices. The control module is configured to determine an active membership of the IMD system comprising each one of the plurality of implantable medical devices that is present in the patient and operable, establish programmable parameters of the IMD system based on the active membership, and control the telemetry module to transmit values for the established programmable parameters to the active membership.

In another example, the disclosure provides a non-transitory, computer-readable storage medium comprising a set of instructions that when executed cause a control module of an external device that is configured for bi-directional communication with a plurality of implantable medical devices to determine an active membership of an implantable medical device (IMD) system, wherein the active membership comprises each one of the plurality of implantable medical devices that is present in a patient and operable; establish programmable parameters for the IMD system based on the active membership; and transmit values for the established programmable parameters to the active membership.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

FIG. 10 is an example of a look-up table that an external programmer may store and use for establishing programmable parameters based on active members of an IMD system present in a patient.

DETAILED DESCRIPTION

Figure 1:
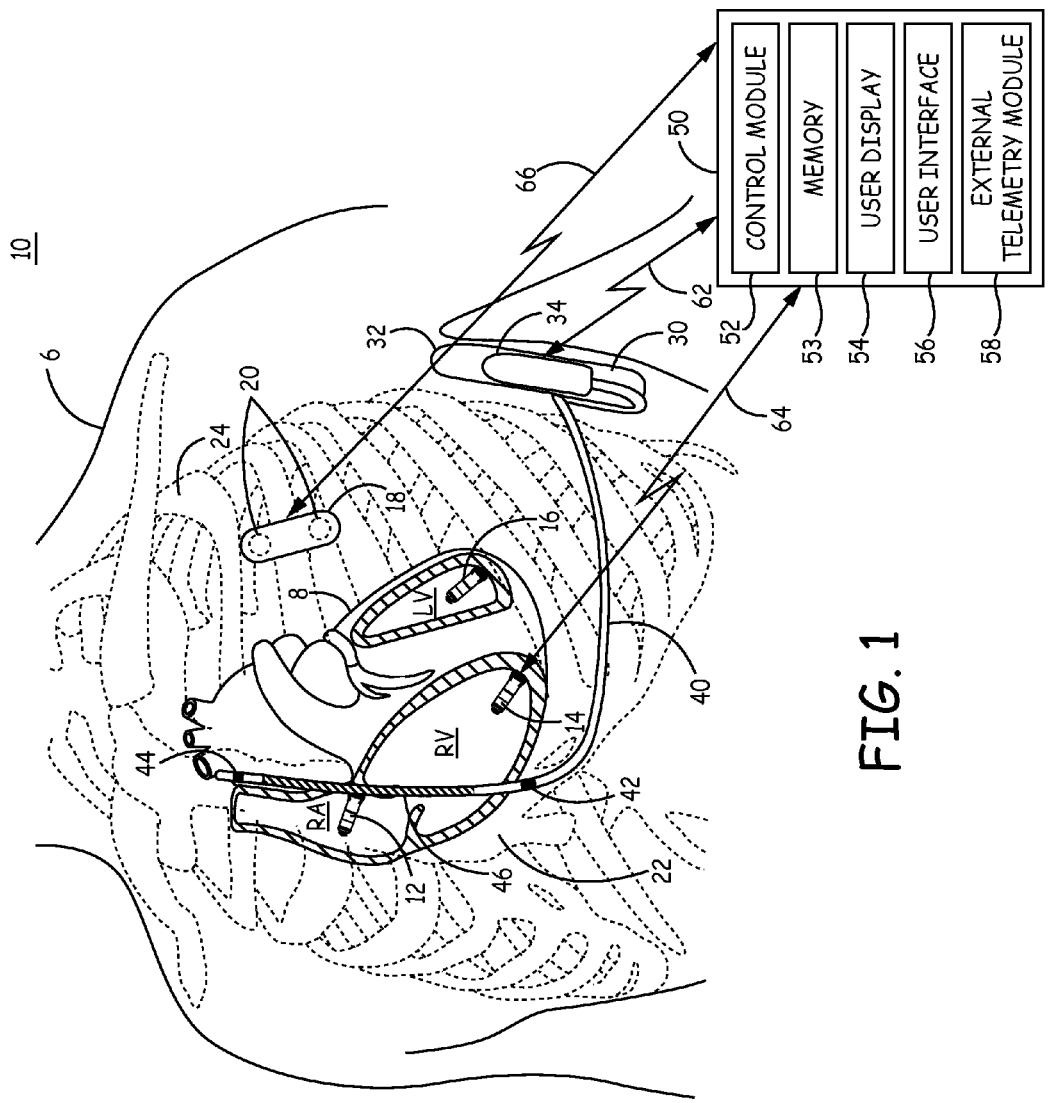
FIG. 1 is a conceptual diagram illustrating an IMD system according to one example.

FIG. 1 is a conceptual diagram illustrating an IMD system 10 according to one example. IMD system 10 includes an external programmer 50 that is configured to recognize the IMDs present in a patient 6 as IMD system members and establish available programmable parameters for each IMD system member based on the presence (or absence) of other IMD system members. IMD system 10 is shown to include multiple IMDs 12, 14, 16, 18 and 30 that may be used to sense cardiac electrical signals and/or provide electrical stimulation therapy to a patient's heart 8. IMD system members 12, 14, 16, 18 and 30 may include sensors for sensing physiological signals other than cardiac electrical signals. Each member 12, 14, 16, 28 and 30 may be capable of monitoring one or more physiological signals and/or deliver one or more therapies for treating abnormal heart rhythms.

Programming techniques disclosed herein may be implemented in other multi-device IMD systems and are not limited to an IMD system 10 provided for monitoring a patient's heart 8 and delivering cardiac electrical stimulation therapies. In other examples, techniques disclosed herein may be implemented in IMD systems provided for monitoring and/or delivering therapy to other organs or tissues in the patient's body. Such systems may include IMDs capable of delivering neurostimulation and/or a pharmacological or biological agents and may monitor functions and treat abnormalities of the central or peripheral nervous system, muscular system, digestive system, or other systems, organs or tissues.

IMD system 10 is shown to include a right atrial (RA) intracardiac pacemaker 12, a right ventricular (RV) intracardiac pacemaker 14, a left ventricular (LV) intracardiac pacemaker 16, an implantable cardiac monitor 18, and an ICD 30. Pacemakers 12, 14, and 16 may be configured to sense cardiac electrical signals and deliver cardiac pacing therapies, e.g., bradycardia pacing, anti-tachycardia pacing, post-shock pacing, and/or cardiac resynchronization therapy (CRT) according to programmed therapy delivery control parameters. Cardiac monitor 18 may be a monitoring-only device for sensing and storing electrocardiogram (ECG) signals for diagnostic purposes without having therapy delivery capabilities. ICD 30 and lead 40 connected thereto is configured to sense cardiac electrical signals for detecting tachyarrhythmia and delivering electrical stimulation therapy for terminating a detected tachyarrhythmia, e.g., a cardioversion or defibrillation shock, and may be configured to deliver post-shock pacing for treating post-shock asystole or bradycardia.

Pacemakers 12, 14 and 16 are shown as transcatheter, intracardiac pacemakers adapted for implantation wholly within a heart chamber, e.g., wholly within the RV, wholly within the left ventricle (LV), wholly within the RA or wholly within the left atrium (LA) of heart 8. In the example of FIG. 1, RA pacemaker 12 is positioned along an endocardial wall of the RA, e.g., along the RA lateral wall or RA septum. RV Pacemaker 14 is positioned along an endocardial wall of the RV, e.g., near the RV apex, and LV pacemaker 16 is positioned along the endocardial wall of the LV, e.g., along the lateral wall. Pacemakers 12, 14, and 16 are reduced in size compared to subcutaneously implanted pacemakers and are generally cylindrical in shape to enable transvenous implantation via a delivery catheter.

The techniques disclosed herein, however, are not limited to the pacemaker locations shown in the example of FIG. 1. In other examples, pacemakers 12, 14 and 16 may be positioned at any other location inside or outside heart 8. For example, any of pacemakers 12, 14 and 16 may be positioned at epicardial or pericardial locations of the respective RA, RV or LV chambers of heart 8.

Pacemakers 12, 14 and 16 are each capable of producing electrical stimulation pulses, i.e., pacing pulses, delivered to respective RA, RV and LV chambers of heart 8 via one or more electrodes on the outer housing of the pacemaker 12, 14 or 16. RA pacemaker 12 is configured to sense an intracardiac electrogram (EGM) signal in the RA and deliver RA pacing pulses using a pair of housing based electrodes. RV pacemaker 14 is configured to sense an EGM signal in the RV and deliver RV pacing pulses using a pair of housing based electrodes. Likewise, LV pacemaker 16 is configured to sense an intracardiac LV EGM signal and deliver LV pacing pulses using a pair of housing based electrodes. Pacemakers 12, 14 and 16 may correspond to a leadless intracardiac pacemaker as generally disclosed in commonly assigned U.S. Pub. No. 2014/0121719 (Bonner et al.), incorporated herein by reference in its entirety.

ICD 30 is illustrated as being implanted near a midaxillary line of patient 6, but may be implanted at other subcutaneous locations of patient 6. ICD 30 is shown connected to a subcutaneous defibrillation lead 40 which may carry a pair of sensing electrodes 42 and 44 for sensing cardiac electrical signals for detecting tachyarrhythmias of heart 8 and a defibrillation electrode 46, which may be an elongated coil electrode, for delivering high voltage cardioversion/defibrillation shock pulses to heart 8 in response to detecting tachycardia or fibrillation.

Lead 40 may extend medially from ICD 30 toward sternum 22 of patient 6. At a location near the xiphoid process, defibrillation lead 40 bends or turns and extends subcutaneously superior, substantially parallel to sternum 22 such that a therapy vector between defibrillation electrode 44 and a second electrode (such the housing 32 of ICD 30) is substantially across a portion of heart 8. Lead 40 may be advanced suprasternally remaining external to the thoracic cavity. In other examples, lead 40 may be advanced substernally or within ribcage 24, e.g., intra-thoracically in direct contact with heart 8, not in direct contact with heart 8, or transvenously within the vasculature of patient 6, e.g., transvenously into heart 8. ICD 30 and lead 40 may correspond to ICD and lead systems as generally disclosed in U.S. patent application Ser. No. 14/198,058 (Olson) and U.S. Pat. No. 8,532,785 (Crutchfield, et al.), both hereby incorporated herein by reference in its entirety.

Cardiac monitor 18 includes housing-based electrodes 20 for sensing a subcutaneous ECG signal for use in diagnosing a cardiac condition. Cardiac monitor 18 may correspond to the REVEAL® Insertable Loop Recorder, available from Medtronic, Inc., Minneapolis, Minn. In other example IMD systems, a hemodynamic monitor may be included that includes a pressure sensor, heart sound sensor, oxygen sensor, and/or other physiological sensors used for monitoring cardiac hemodynamic function for diagnosing a patient condition and guiding therapy decisions. Another example of a cardiac monitoring device is generally disclosed in commonly-assigned U.S. Pat. No. 6,599,250 (Webb, et al.), incorporated herein by reference in its entirety.

Depending on individual patient need, patient 6 may receive any one or combination of IMDs 12, 14, 16, 18 and 30 first with additional ones of IMDs 12, 14, 16, 18 and 30 being implanted at later dates. For example, a patient may receive cardiac monitor 18 first to assess a need for a pacemaker or ICD. The patient may receive RA pacemaker 12 next to provide bradycardia pacing. RV pacemaker 14 may be implanted at a later time after the patient develops a need for ventricular pacing, e.g., if the patient develops AV conduction defects. If the patient is determined to be at risk of experiencing ventricular tachyarrhythmia, the patient may receive ICD 30. At some point, the patient may present ventricular asynchrony leading to hemodynamic insufficiency and receive LV pacemaker 16 for delivering LV pacing to re-establish ventricular synchrony. In other examples, the patient may receive any combination of two or more of IMDs 12, 14, 16, 18 and 30 during the same implant procedure. It is recognized that a patient may never receive all of the IMD system members 12, 14, 16, 18 and 30 depending on patient need and the particular combination of IMDs 12, 14, 16, 18 and 30 shown in FIG. 1 is provided to illustrate one possible multi-device IMD system 10. Numerous variations and combinations of a multi-device IMD system implanted in a patient may be used according to patient need that may or may not include the particular devices shown in FIG. 1. For example, another IMD system implanted in a patient may include a neurostimulator delivering phrenic nerve stimulation or vagal nerve stimulation.

Each IMD 12, 14, 16, 18 and 30 is capable of bidirectional wireless communication with an external programmer 50. External programmer 50 may be used by a clinician or other user in a medical facility, such as a clinic, hospital, emergency room, or operating theater, for interrogating and programming each respective IMD 12, 14, 16, 18 and 30. In other examples, external programmer 50 may be a home monitor located in a patient's home, or a handheld device. Some aspects of external programmer 50 may correspond to the external programming/monitoring unit disclosed in U.S. Pat. No. 5,507,782 (Kieval, et al.), hereby incorporated herein by reference in its entirety.

External programmer 50 establishes a wireless radio frequency (RF) communication link 62, 64, 66 with ICD 30, cardiac monitor 18, and pacemaker 14, respectively, using a communication protocol that appropriately addresses the targeted IMD 30, 18 or 14. External programmer 50 is further capable of establishing wireless RF communication links with pacemakers 12 and 16, which are not shown in FIG. 1 for the sake of clarity. One example of an RF telemetry communication system that may be implemented in system 10 is generally disclosed in U.S. Pat. No. 5,683,432 (Goedeke, et al.), incorporated herein by reference in its entirety.

External programmer 50 may be used for retrieving data from and sending programming data to IMDs 12, 14, 16, 18 and 30. Examples of retrieved data may include currently programmed control parameters, physiological signals such as RA, RV, and/LV EGM signals, ECG signals, tachyarrhythmia episode data, therapy delivery data such as a history of pacing frequency and shock delivery, and results of device diagnostic testing.

Data sent to IMDs 12, 14, 16, 18 and 30 may include programmable control parameters which are established by external programmer 50 upon recognizing the IMD system members that are present in patient 6. As described below, the user may select a device-specific programmable parameter setting that is transmitted to the target IMD by programmer 50. In other instances, the user may select a system programmable parameter that results in multiple parameter settings being transmitted to multiple IMDs 12, 14, 16, 18 and/or 30 as needed to enable coordinated behavior of each IMD 12, 14, 16, 18 and 30 for providing a particular monitoring or therapy delivery function without competition, undesired redundancy or conflict between implanted IMDs 12, 14, 16, 18 and/or 30.

IMDs 12, 14, 16, 18 and 30 may or may not be configured to communicate directly with each other. For example, pacemakers 12, 14 and 16 may or may not be configured to initiate an RF communication session with one another. Pacemakers 12, 14 and 16 may be configured to periodically "listen" for a valid "wake up" telemetry signal from external device 50 and optionally ICD 30 and/or monitor 18 and power up their own telemetry module to establish a communication link, e.g., link 64, in response to a valid telemetry signal (or go back to "sleep" if no valid telemetry signal is received). However, pacemakers 12, 14 and 16 may not be configured to transmit a "wake up" signal to another implanted IMD 18 or 30 to initiate a communication session. In other examples, the IMDs 12, 14, 16, 18 and 30 may be configured to communicate with each other. In order to conserve battery life of the implanted devices, intra-IMD communication may be minimized.

External programmer 50 includes an external control module 52, memory 53, user display 54, user interface 56 and telemetry module 58. External control module 52 controls external programmer operations and processes data and signals received from IMDs 12, 14, 16, 18 and 30. According to techniques disclosed herein, external control module 52 may send a telemetry wake-up signal to IMDs 12, 14, 16, 18 and 30 and recognize and identify the IMD system members present in patient 6 based on response signals transmitted from the individual IMDs 12, 14, 16, 18 and 30 upon receipt of the wake-up signal.

External programmer 50 establishes an IMD system membership as being the IMDs that are present and active in the patient at a given time based on which IMDs 12, 14, 16, 18 and/or 30 respond to a wake-up or query signal. As such, while programmer 50 is capable of communicating with the various IMDs 12, 14, 16, 18 and 30 and all are illustrated as being implanted in patient 6 in FIG. 1, all of IMDs 12, 14, 16, 18 and 30 may not be active IMD system members at a given time. The IMD system membership may change over time as IMDs 12, 14, 16, 18 and/or 30 are added or removed from patient 6 according to patient need, battery end-of-life, or other reasons. In some cases, an IMD 12, 14, 16, 18 or 30 may be physically removed from the patient but in other cases an IMD may reach battery end-of-life or be "turned off" such that it is no longer active or functional in the implanted IMD system 10. As used herein, the terms "IMD system members" refers to any of the IMDs 12, 14, 16, 18 and/or 30 that are identified by external programmer 50 as being implanted, or about to be implanted, in the patient 6 and operable (i.e., not reached battery end-of-life or otherwise "off" or not functioning). The "active membership" of the IMD system, therefore, includes each one of the IMDs 12, 14, 16, 18, and/or 30 that is present in the patient 6. In some cases, querying and programming of IMD system members may occur during an implantation procedure just prior to implanting one or more of the IMD system members. In other cases querying and programming of the IMD system members may occur after all members are implanted. As such, in some examples, the active membership including each of the IMDs 12, 14, 16, 18 and/or 30 that are "present in the patient" is intended to be inclusive of the IMDs that are already implanted in the patient and the IMDs 12, 14, 16, 18 and/or 30 that are in the vicinity of the patient and ready to be programmed and implanted. Telemetry signal responses from the IMDs present and functioning allows the external programmer 50 to recognize and identify the IMD system members 12, 14, 16, 18 and/or 30 and establish the programmable parameters presented to a user for programming the IMD system 10 based on the IMD system membership.

Each IMD 12, 14, 16, 18 and 30 may transmit a unique identification with each data packet transmitted to external programmer 50 so that programmer 50 can recognize and identify each active and implanted IMD system member that is transmitting data and track which data came from which IMD. Likewise, an IMD 12, 14, 16, 18 or 30 only accepts a data packet transmitted from external programmer 50 if the data packet is addressed to the respective IMD identification and does not accept any data packets addressed to a different IMD.

External control module 52 may provide user display 54 with data for generating a display, which may be a graphical user interface, to a user for selecting and programming control parameters used by each of the implanted and active IMDs 12, 14, 16, 18 and/or 30. The user display 54 may be a graphical user interface that presents one or more programming screens specific to a single one of the IMD system members 12, 14, 16, 18 and/or 30 present in patient 6. The user may be able to select among various programming screens that are specific to the different IMD system members 12, 14, 16, 18 and/or 30. For example, the user may be able to select from a tachyarrhythmia therapy screen that is specific to programming control parameters in ICD 30 and a bradycardia therapy screen that is specific to programming control parameters in RA pacemaker 12.

In other examples, various device-specific programming screens may be merged as system programming screens that are not device-specific. External control module 52 may be configured to control external telemetry module 58 to transmit programming commands to the appropriate IMD system members 12, 14, 16, 18 and/or 30 in response to user input without requiring user knowledge as to which device(s) is/are receiving programming commands and which devices are implementing particular programmed control parameters. For example, a bradycardia therapy programming menu may be displayed that enables a user to program various parameters that will be appropriately transmitted to the correct pacemaker 12, 14, or 16 as needed. A tachyarrhythmia therapy programming menu may be displayed that enables a user to program various parameters that are appropriately transmitted to pacemakers 12, 14, 16 and/or ICD 30 as needed without requiring the user to enter a device-specific programmable parameter in some cases.

External programmer 50 may display other data and information relating to IMD system functions to a user for reviewing IMD system operation and programmed parameters as well as EGM signals, ECG signals, or other physiological signals or data that are retrieved from the active IMD system members 12, 14, 16, 18 and/or 30 during an interrogation session. User interface 56 may include a mouse, touch screen, keyboard and/or keypad to enable a user to interact with external programmer 50 to initiate a telemetry session with IMD system members 12, 14, 16, 18 and/or 30 for retrieving data from and/or transmitting data to members 12, 14, 16, 18 and/or 30 for selecting and programming sensing and therapy delivery control parameters.

Communication links, e.g., links 62, 64 and 66, may be established between IMD members 12, 14, 16, 18 and/or 30 and external programmer 50 using a radio frequency (RF) link, for example in the Medical Implant Communication Service (MICS) band, Medical Data Service (MEDS) band, BLUETOOTH® or Wi-Fi. External telemetry module 58 is configured for bidirectional communication with an implantable telemetry module included in each of IMDs 12, 14, 16, 18 and 30. External telemetry module 58 establishes a wireless RF communication link, e.g., link 62, 64 or 66, with IMD system members 12, 14, 16, 18 and/or 30 using a communication protocol that appropriately addresses the targeted active IMD system members 12, 14, 16, 18 and/or 30. External programmer 50 may be capable of maintaining multiple communication links, e.g., links 62, 64 and 66, for simultaneous communication with IMD system members 12, 14, 16, 18 and/or 30. One example of a telemetry system that allows multiple communication links to coexist, which may be implemented in IMD system 10, is generally disclosed in the above-incorporated U.S. Pat. No. 5,843,139 (Goedeke, et al.).

In some examples, external telemetry module 58 is configured for multi-channel communication with multiple IMD system members 12, 14, 16, 18 and/or 30 simultaneously using different communication protocols and/or different modulation schemes for each of the communication channels. In this case, the multi-channel communication telemetry module 50 enables multiple communication links, e.g., links 62, 64 and 66, to be maintained concurrently for transmitting and receiving data to/from multiple IMD system members 12, 14, 16, 18 and/or 30. An example of a multi-channel communication network and associated methods is generally disclosed in commonly-assigned U.S. Pat. No. 7,742,816 (Masoud, et al.), incorporated herein by reference in its entirety.

The IMD system members 12, 14, 16, 18 and/or 30 may communicate with external programmer 50 on separate frequency channels, using frequency hopping, time slicing, or other methods for reducing interference while transmitting and receiving during a telemetry session. After establishing a communication link, external programmer 50 may assign each IMD system member 12, 14, 16, 18 and/or 30 to a frequency channel so that each member monitors that frequency channel for communication from programmer 50. In some cases, each IMD system member 12, 14, 16, 18 and/or 30 may be configured to communicate with programmer 50 using different telemetry protocols that use different frequencies and schemes that do not significantly interfere with each other.

In other examples, one IMD system member 12, 14, 16, 18 or 30 is selected as a "master" IMD that recognizes and identifies each of the other IMD system members. The "master" IMD transmits the IMD system membership to the external programmer 50. The "master" may control coordinated communication between external programmer 50 and the IMD system members 12, 14, 16, 18 and/or 30, e.g., according to designated communication time slots. Reference is made, for example, to U.S. Pat. No. 8,102,789 (Rosar, et al.), incorporated herein by reference in its entirety.

External telemetry module 58 may be capable of bi-directional communication with IMD system members 12, 14, 16, 18 and/or 30 over a wide range of distances, e.g., up to approximately 10 meters. In other examples, telemetry communication may require the use of a programming head placed in proximity of patient 6, e.g. against or within several centimeters of the patient's skin or clothing, to facilitate data transfer.

It is contemplated that external programmer 50 may be in wired or wireless connection to a communications network via telemetry module 58 for transferring data to a remote database or computer to allow remote management of the patient 6. When programmer 50 is coupled to a communication network, data may be transferred between programmer 50 and a centralized patient management system that includes a central programmer and database. Data may be transferred between a central programmer and database and a remote programmer via a host server which may perform programmable parameter generation, programming command conversion operations and other data processing or operations attributed herein to external programmer 50. An example communication scheme that may be used for remotely programming IMD system 10 using the techniques disclosed herein is generally disclosed in U.S. Pat. No. 6,442,433 (Linberg), incorporated herein by reference in their entirety.

As will be described herein, different functions or control parameter settings for each respective IMD system member 12, 14, 16, 18 and/or 30 identified as being active and implanted in the patient may be enabled or disabled based on which IMDs are present. For example, bradycardia pacing therapies delivered in multiple heart chambers may be enabled when pacing capability in more than one heart chamber is possible due to the presence of more than one intracardiac pacemaker 12, 14 and/or 16. Anti-tachycardia therapies delivered by an intracardiac pacemaker 12, 14 or 16 may be enabled when ICD 30 is present but disabled when ICD 30 is not present.

If a dedicated monitoring device is present such as cardiac monitoring device 18, monitoring and/or physiological signal storage may be reduced in therapy delivery devices such as pacemakers 12, 14 and 16 and ICD 30 to conserve memory, power, and minimize redundant functions. For example, if cardiac monitoring device 18 is present, tachyarrhythmia episode storage capacity may be reduced or disabled in intracardiac pacemakers 12, 14, and 16. If cardiac monitoring device 18 is not present, tachyarrhythmia episode storage may be enabled in an expanded capacity in pacemakers 12, 14, or 16 compared to when cardiac monitoring device 18 is present. For instance, the number of tachyarrhythmia episodes, the duration of stored episodes, and/or the cardiac signal resolution may be increased for storing tachyarrhythmia episodes detected by pacemakers 12, 14 and/or 16. Data relating to a tachyarrhythmia episode detected by more than one IMD, e.g., by monitoring device 18 and ICD 30, may be selected from one IMD or merged from multiple IMDs for generating a single display of the tachyarrhythmia episode data by external programmer 50.

Figure 2:
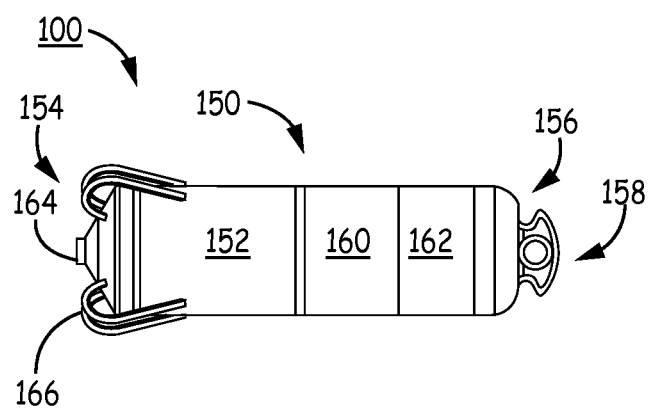
FIG. 2 is a conceptual diagram of an intracardiac pacemaker that may be included in the IMD system of FIG. 1 according to one example.

FIG. 2 is a conceptual diagram of an intracardiac pacemaker 100 that may correspond to RA pacemaker 12, RV pacemaker 14 or LV pacemaker 16 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 154 of pacemaker 100, and electrode 162 is shown as a ring electrode along a mid-portion of housing 150, for example adjacent proximal end 156. Distal end 154 is referred to as "distal" in that it is expected to be the leading end as it advanced through a delivery tool such as a catheter and placed against a target pacing site.

Electrodes 162 and 164 may be positioned on or as near as possible to respective proximal and distal ends 156 and 154 to increase the inter-electrode spacing between electrodes 162 and 164. Electrodes 162 and 164 form a cathode and anode pair for bipolar cardiac pacing and sensing. In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be positioned at locations along pacemaker 100 other than the locations shown. Instead of carrying both electrodes 162 and 164 along housing 150, pacemaker 100 may include an insulated, flexible conductor extending away from housing 150 and carrying one or both of sensing and pacing electrodes 162 and 165, e.g., as disclosed in commonly-assigned U.S. Pub. No. 2013/0035748 (Bonner, et al.), hereby incorporated herein by reference in its entirety.

Housing 150 is formed from a biocompatible material, such as a stainless steel or titanium alloy. In some examples, the housing 150 or a portion thereof may include an insulating coating. Examples of insulating coatings include parylene, urethane, PEEK, or polyimide among others.

Housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position.

Pacemaker 100 may further include a delivery tool interface 158. Delivery tool interface 158 is located at the proximal end 104 of pacemaker 100 and is configured to connect to a delivery device, such as a catheter, used to position pacemaker 100 at an implant location during an implantation procedure, for example within a heart chamber.

Figure 3:
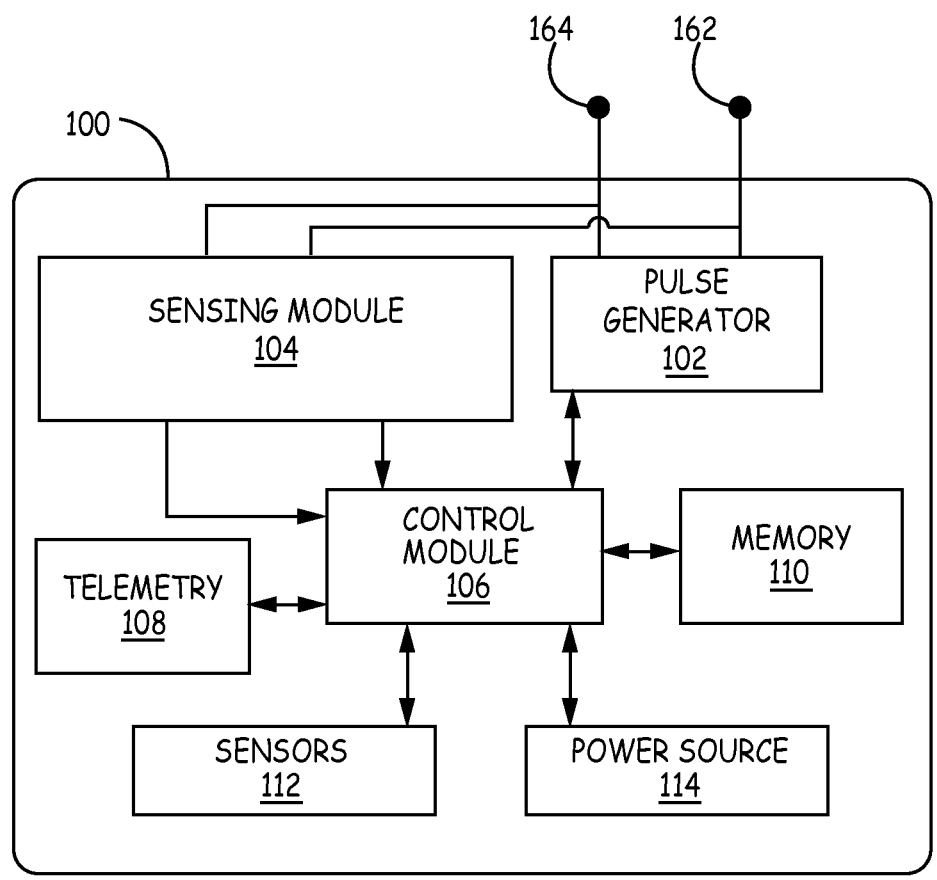
FIG. 3 is a functional block diagram of an example configuration of the pacemaker shown in FIG. 2.

FIG. 3 is a functional block diagram of an example configuration of pacemaker 100 shown in FIG. 2, and may correspond generally to the functional circuitry included in RA pacemaker 12, RV pacemaker 14 and LV pacemaker 16. Pacemaker 100 includes a pulse generator 102, a sensing module 104, a control module 106, memory 110, telemetry module 108 and a power source 114. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality of an IMD system member.

Each of RA pacemaker 12, RV pacemaker 14 and LV pacemaker 16 will include similar modules as represented by the pacemaker 100 shown in FIG. 3, however it is understood that the modules may be configured according to the functionality of the separate RA pacemaker 12, RV pacemaker 14, and LV pacemaker 16 for sensing EGM signals and delivering therapy as needed in the respective heart chambers. For example, when pacemaker 100 is a RA pacemaker 12, control module 106 is enabled to control atrial pacing escape intervals according to cardiac pacing therapies that include atrial pacing. When pacemaker 100 is RV pacemaker 14 or LV pacemaker 16, control module 106 is enabled to control ventricular pacing escape intervals according to cardiac pacing therapies that include RV or LV pacing. Adaptations of the hardware, firmware or software of the various modules necessary to meet the described functionality of the intracardiac pacemakers positioned in different heart is understood to be included in the various modules. The particular form of software, hardware and/or firmware employed to implement the functionality of the IMD system 10 disclosed herein will be determined primarily by the particular system architecture employed in a given IMD and by the particular detection and therapy delivery methodologies employed by the IMD. Providing software, hardware, and/or firmware to accomplish the described functionality in the context of any modern IMD, given the disclosure herein, is within the abilities of one of skill in the art.

The functions attributed to IMDs 12, 14, 16, 18 and 30 herein may be embodied as one or more processors, controllers, hardware, firmware, software, or any combination thereof. Depiction of different features as specific circuitry or modules in the accompanying drawings is intended to highlight different functional aspects and does not necessarily imply that such functions must be realized by separate hardware or software components or by any particular architecture. Rather, functionality associated with one or more modules, processors, or circuits may be performed by separate hardware, firmware, or software components, or integrated within common hardware or software components. For example, pacing control operations performed by pacemaker 100 may be implemented in control module 106 executing instructions stored in memory 110 and relying on input from sensing module 104.

Pulse generator 102 generates electrical stimulation pulses that are delivered to heart tissue via electrodes 162 and 164. In some examples, pulse generator 102 may include one or more capacitors and a charging circuit to charge the capacitor(s) to a programmed pacing pulse voltage. At appropriate times, as controlled by a pace timing and control circuit included in control module 106, the capacitor is coupled to pacing electrodes 162 and 164 to discharge the capacitor voltage and thereby deliver the pacing pulse. Pacing circuitry generally disclosed in the above-incorporated U.S. Pat. No. 8,532,785 (Crutchfield, et al.) and in U.S. Pat. No. 5,597,782 (Kieval, et al.), incorporated herein by reference in its entirety, may be implemented in pacemaker 100 for charging a pacing capacitor to a predetermined pacing pulse amplitude under the control of control module 106 and delivering a pacing pulse.

Control module 106 controls pulse generator 102 to deliver a pacing pulse in response to expiration of a pacing timing interval according to programmed therapy control parameters stored in memory 110. At least one programmable control parameter used by control module 106 is programmed upon receipt of a command from external programmer 50 that has been established based on the IMD system members present in the patient. The programmable control parameter may be programmed automatically by external programmer 50 based on the presence or absence of one or more other IMD system members. In other cases, the programmable control parameter is user-programmable parameter that is displayed to a user on user display 54 (FIG. 1) to allow the user to select and program the control parameter value. The display of the programmable control parameter to a user (or its available settings) is based on the recognition of IMD system members 12, 14, 16, 18 and/or 30 by programmer 50.

Different programmable parameters may be made available depending upon which of pacemakers 12, 14, and 16 are present. In some cases, additional pacing modes and associated parameters are available for programming (either automatically by programmer 50 or in response to user input) when two or more pacemakers are present, e.g. RA pacemaker 12 and RV pacemaker 14, than when either pacemaker is present alone. For example, when RA pacemaker 12 is present alone, available pacing modes may include AAI and AAIR in which atrial pacing and atrial sensing are enabled in either a non-rate responsive or rate-responsive manner. If RV pacemaker 14 is present, ADI and ADIR pacing modes may be made available to enable sensing of far field R-waves (dual chamber sensing) for coordinating functions of RA pacemaker 12 and RV pacemaker 14. As such, establishing programmable parameters by external programmer 50 when two (or more) IMDs 12, 14, 16, 18 and/or 30 are present in the IMD system membership may be more than adding a first set of parameters available for one IMD when implanted alone to a second set of parameters available for the second IMD when it is implanted alone. Additional programmable parameters for the first IMD may be made available due to the presence of the second IMD that are not available if the first IMD is implanted without the second IMD. Other illustrative examples of this situation are described below.

The pace timing and control circuit included in control module 106 sets various timing intervals, often referred to as escape intervals, used for controlling the timing of pacing pulses relative to a paced or sensed event. Upon expiration of a pacing timing interval, a pacing pulse is delivered. If a cardiac event is sensed during the pacing timing interval, the scheduled pacing pulse may be inhibited, and the pacing timing interval may be restarted. Pacing escape intervals available for programming may be established by programmer 50 based on which pacemakers 12, 14, and/or 16 are present. For example, a paced atrioventricular (AV) interval may be added to the available programmable parameters for RV pacemaker 14 or LV pacemaker 16 if RA pacemaker 12 is present.

Sensing module 104 includes cardiac event detectors for receiving cardiac EGM signals developed across electrodes 162 and 164. A cardiac event is sensed by sensing module 104 when the EGM signal crosses a sensing threshold, which may be an auto-adjusting sensing threshold, of a cardiac event detector. In response to a threshold crossing, sensing module 104 passes a sensed event signal to control module 106. RA pacemaker 12 may be programmed with a sensing threshold appropriate for sensing P-waves attendant to the depolarization of the atria. RV and LV pacemakers 14 and 16 may be programmed with a sensing threshold appropriate for sensing R-waves attendant to the depolarization of the ventricles.

Sensing module 104 may include multiple sensing channels for intentionally sensing both near field (NF) events (occurring in the heart chamber in which the pacemaker 100 is implanted) and far-field (FF) events (occurring in a heart chamber other than the chamber in which pacemaker 100 is implanted. Sensed events may include NF and FF intrinsic events, NF and FF evoked events, and FF pacing pulse events. By intentionally sensing FF events, control module 106 can control pacemaker 100 to operate in a coordinated manner with a pacemaker in another heart chamber.

For example, the sensing module 104 in RV pacemaker 14 or LV pacemaker 16 may include a NF sensing channel for sensing NF R-waves and a FF sensing channel for sensing FF atrial pacing pulses delivered by RA pacemaker 12 and/or FF P-waves. The sensing module 104 of RA pacemaker 12 may include a NF sensing channel for sensing NF P-waves and a FF sensing channel for sensing far-field R-waves or ventricular pacing pulses. Programmer 50 may establish which sensing channels are enabled, which sensing thresholds are programmable, and what other sensing control parameters are programmable in one pacemaker 12, 14, or 16 based on which other ones of pacemakers 12, 14 and 16 are present in the IMD system membership.

In response to a sensing threshold crossing, sensing module 104 may pass sense event signals to control module 106. Control module 106 uses the sense event signals to control pulse generator 102 in a desired pacing mode. The pacing mode may be controlled according to control parameters programmed in memory 110 by external programmer 50 based on the IMD system members 12, 14, 16, 18 and 30 that are present in the patient.

Memory 110 of pacemaker 100 (and memory 82 of ICD 30 shown in FIG. 4) may include computer-readable instructions that, when executed by control module 106 or ICD control module 80, respectively, cause the control modules 106 or 80 to perform various functions attributed throughout this disclosure to pacemakers 12, 14, or 16 or ICD 30, respectively. The computer-readable instructions may be encoded within memory 110 or memory 82. Memory 110 and memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 110 may store timing intervals, counters, or other data used by control modules 106 and 80 to control the delivery of pacing pulses by pulse generator 102 according to programmed therapy delivery parameters.

Pacemaker 100 may further include other physiological sensors 112 producing physiological signals for monitoring patient 6. For example, sensors 112 may include an accelerometer for producing a patient activity signal passed to control module 106 for use in controlling rate responsive pacing. In other examples, sensors 112 may include an acoustical sensor for sensing heart sounds, a blood pressure sensor, or an oxygen sensor among other implantable physiological sensors.

Power source 114 provides power to each of the other modules and components of pacemaker 100 as required. Control module 106 may execute power control operations to control when various components or modules are powered to perform various pacemaker functions. Power source 114 may include one or more energy storage devices, such as one or more rechargeable or non-rechargeable batteries. The connections between power source 114 and other pacemaker modules and components are not shown in FIG. 3 for the sake of clarity.

Telemetry module 108 includes a transceiver and associated antenna for transferring and receiving data via a radio frequency (RF) communication link with external programmer 50 as described above. Telemetry module 108 responds to a wake up signal or system query from external programmer 50. This response allows external programmer 50 to identify and recognize pacemaker 100 as an IMD system member and, based on which other IMD system members 12, 14, 16 18 and/or 30 are implanted in patient 6, external programmer 50 may automatically establish programmable parameters that are displayed to a user for programming pacemaker 100.

Figure 4:
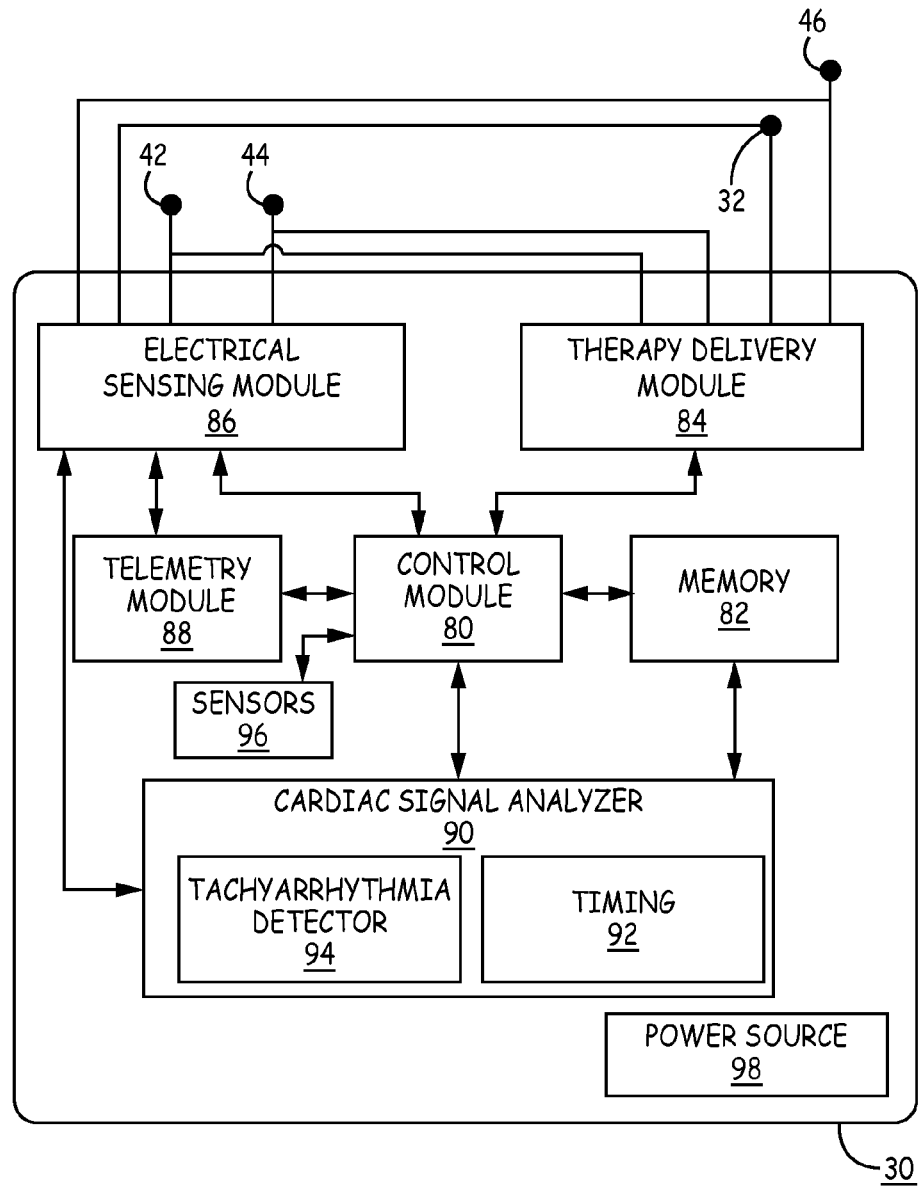
FIG. 4 is a conceptual diagram of an ICD that may be included in the IMD system of FIG. 1 according to one example.

FIG. 4 is a conceptual diagram of ICD 30 according to one example. The electronic circuitry enclosed within housing 32 (shown as a housing electrode 32 in FIG. 4) includes software, firmware and hardware that cooperatively monitor one or more ECG signals, determine when a cardioversion-defibrillation shock is necessary, and deliver prescribed cardioversion-defibrillation therapies. In some examples, ICD 30 may be coupled to a lead, such as lead 40, carrying electrodes, such as electrodes 42, 44 and 46, positioned in operative relation to the patient's heart for delivering cardiac pacing pulses, e.g., post-shock bradycardia pacing, in addition to shock therapies.

ICD 30 includes control module 80, memory 82, therapy delivery module 84, electrical sensing module 86, telemetry module 88, and cardiac signal analyzer 90. A power source 98 provides power to the circuitry of ICD 30, including each of the modules 80, 82, 84, 86, 88, and 90 as needed. Power source 98 may include one or more energy storage devices, such as one or more rechargeable or non-rechargeable batteries.

The functional blocks shown in FIG. 4 represent functionality that may be included in ICD 30 and may include any discrete and/or integrated electronic circuit components that implement analog and/or digital circuits capable of producing the functions attributed to ICD 30 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 42, 44, and 46 carried by lead 40 (shown in FIG. 1) and housing 32, which may serve as a common or ground electrode.

Electrical sensing module 86 is selectively coupled to electrodes 42 and 44 and housing 32 in order to monitor electrical activity of the patient's heart. Electrical sensing module 86 may additionally be selectively coupled to electrode 46. Sensing module 86 is enabled to selectively monitor one or more sensing vectors selected from the available electrodes 42, 44, 46 and housing 32. For example, sensing module 86 may include switching circuitry for selecting which of electrodes 42, 44, 46 and housing 32 are coupled to sense amplifiers included in sensing module 86. Switching circuitry may include a switch array, switch matrix, multiplexer, or any other type of switching device suitable to selectively couple sense amplifiers to selected electrodes. In some examples, electrical sensing module 86 includes multiple sensing channels for sensing multiple ECG sensing vectors selected from electrodes 42, 44, 46 and housing 32.

Each sensing channel may include cardiac event detection circuitry for sensing cardiac events from the received ECG signal developed across the selected electrodes 42, 44, 46 and housing 32. Each sensing channel may produce a sense event signal that is passed to control module 80 and/or cardiac signal analyzer 90 when a received ECG signal crosses the respective auto-adjusting cardiac event sensing threshold. For example, R-wave sense event signals may be passed to tachyarrhythmia detector 94 and timing circuit 92 of cardiac signal analyzer 90 when a received ECG signal crosses an auto-adjusting R-wave sensing threshold.

Sense event signals produced by sensing module 86 may be used by tachyarrhythmia detector 94 for detecting shockable heart rhythms or by timing circuit 92 for synchronizing cardioversion shocks delivered by therapy delivery module 84 with sensed R-waves. Sensing module 86 may include an analog-to-digital converter for providing a digital ECG signal to control module 80 and/or cardiac signal analyzer 90. For example one or more ECG signals received by sensing module 86 may each be converted to a multi-bit digital signal by sensing module 86 and provided to tachyarrhythmia detector 94 for performing ECG morphology analysis used for detecting a shockable heart rhythm.

Cardiac signal analyzer 90 includes a tachyarrhythmia detector 94 for detecting and discriminating shockable tachyarrhythmia episodes. Cardiac signal analyzer 90 may further include a timing circuit 92 that includes various timers and/or counters for measuring time intervals, such as RR intervals, and setting time segments or windows such as morphology template windows, morphology analysis windows relative to R-wave sense event signals, cardiac signal analysis time segments, or for performing other timing related functions of cardiac signal analyzer 90 including synchronizing cardioversion shocks or other therapies delivered by therapy delivery module 84 with sensed cardiac events.

The timing of R-wave sense event signals received from sensing module 86 is used by timing circuit 94 to determine RR intervals between sense event signals. Tachyarrhythmia detector 94 may count RR intervals measured by timing circuit 92 that fall into different rate detection zones for determining a ventricular rate or performing other rate- or interval-based assessment for detecting ventricular tachyarrhythmia and discriminating shockable from non-shockable rhythms. Tachyarrhythmia detection algorithms may utilize not only ECG signal analysis methods but may also utilize supplemental sensors 96, such as blood pressure, tissue oxygenation, respiration, patient activity, heart sounds, and the like, for contributing to a decision by control module 80 to apply or withhold a therapy.

Examples of ICDs that may be included in IMD system 10 or algorithms that may be performed by ICD 30 for detecting, discriminating and treating shockable rhythms, are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. The detection algorithms are highly sensitive and specific for the presence or absence of life threatening, shockable ventricular tachycardia (VT) and ventricular fibrillation (VF).

Therapy delivery module 84 includes a high voltage (HV) therapy delivery module including one or more HV output capacitors and, in some instances, a low voltage therapy delivery module. When a malignant tachycardia is detected the HV capacitors are charged to a pre-programmed voltage level by a HV charging circuit.

ECG episode data related to the detection of VT or VF and the delivery of a cardioversion or defibrillation shock may be stored in memory 82 and transmitted by telemetry module 88 to programmer 50 upon receipt of an interrogation command. Clinician review of episode data facilitates diagnosis and prognosis of the patient's cardiac state and therapy management decisions, including selecting programmable control parameters used for detecting shockable rhythms and delivering therapy.

Programmable control parameters used by control module 80 for controlling sensing and therapy delivery functions of ICD 30 may be programmed into memory 82 via telemetry module 88. Telemetry module 88 includes a transceiver and antenna for communicating with programmer 50 (shown in FIG. 1) using RF communication as described above. Under the control of control module 80, telemetry module 88 may receive downlink telemetry from and send uplink telemetry to programmer 50. As described below, ICD 30 may be configured to transmit a response signal to a system query received from programmer 50 for establishing IMD system membership. In some examples, ICD 30 may function as a "master" device for channeling communication signals between IMD system members and programmer 50. For example, ICD 30 may receive identity signals transmitted from other IMD system members 12, 14, 16, and/or 18 and transmit the IMD system membership to programmer 50.

Figure 5:
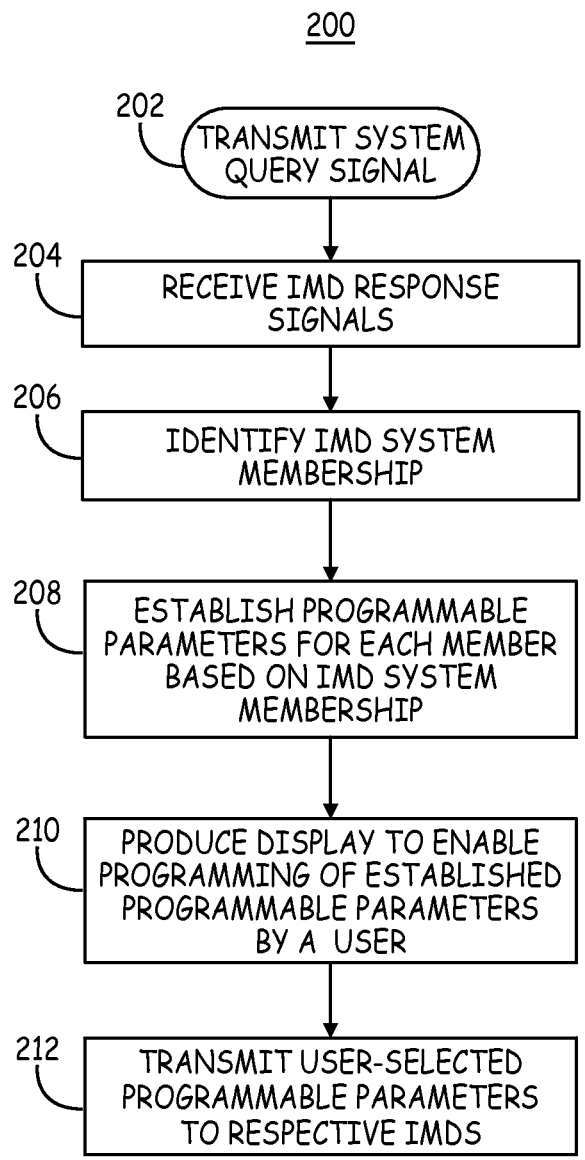
FIG. 5 is a flow chart of a method for programming an IMD system based on an active membership of IMDs implanted in a patient, such as the system shown in FIG. 1.

FIG. 5 is a flow chart 200 of a method for programming an IMD system, such as the system 10 shown in FIG. 1, based on an active membership of IMDs implanted in a patient. At block 202, the external programmer 50 transmits a query signal to wake-up and interrogate devices implanted and functional in the patient. In various examples, the query signal may be a wake-up signal received simultaneously by all IMDs that may be implanted in the patient, an IMD-specific signal that is transmitted to detect the presence of a specific IMD system member, or sequential signals transmitted to detect the presence of each IMD system member.

At block 204, the IMD system members 12, 14, 16, 18 and/or 30 transmit a response signal to external programmer 50. The response signal may include IMD identification data, e.g., identifying the type and model number of the IMD sending the response signal. The external programmer 50 receives the response signals from each IMD system member 12, 14, 16, 18 and/or 30 and identifies the active system members implanted in the patient at block 206. In other examples, one IMD system member 12, 14, 16, 18 or 30 acts as a "master" that detects other IMD system members present in the patient and transmits a response signal to external programmer 50 that identifies all of the system members 12, 14, 16, 18 and/or 30 that are present and active.

In other examples, programmer 50 identifies the IMD system members 12, 14, 16, 18 and/or 30 at block 306 based on user input. A user may manually enter the IMD system members present, e.g., by interacting with user interface 54 to select available IMDs from one or more lists, tables, or drop-down menus presented to the user on user display 54.

At block 208, the programmer 50 establishes the programmable parameters for each IMD system member 12, 14, 16, 18 and/or 30 based on the IMD system membership. In some examples, programmer memory 53 stores tables of programmable features and parameters that are available depending on the IMD system membership.

For example, RV pacemaker 14 and/or LV pacemaker 16 may be capable of delivering anti-tachycardia pacing (ATP), but ATP therapies delivered by RV or LV pacemaker 14 or 16 may be made available only if ICD 30 is present. If at least one of RV pacemaker 14 or LV pacemaker 16 is present and ICD 30 is present, external programmer 50 may establish that programmable ATP therapy control parameters are available for RV pacemaker 14 or LV pacemaker 16. If ICD 30 is not present, ATP therapy control parameters are not available for programming by a user and are not displayed by programmer 50. Programmable ATP therapy control parameters may include the type of ATP therapy delivered (ramp, burst, etc.), pulse amplitude, number of pulses, etc.

In another example, RA pacemaker 12 may be capable of detecting atrial tachyarrhythmia and delivery atrial ATP therapy. However, programmer 50 may establish programmable parameters for controlling atrial tachyarrhythmia detection and/or atrial ATP therapy delivery only when at least one of RV pacemaker 14 or LV pacemaker 16 is present.

In some cases, a programmable parameter established by programmer 50 based on IMD system membership is not a user-programmable parameter. Programmer 50 may automatically program a parameter to a desired setting, or enable or disable a feature or function of an IMD 12, 14, 16, 18 or 30, based on the IMD system membership without requiring or enabling user input via a user display. For example, programmer 50 may enable a specific sensing mode or change a bandpass filter or blanking interval of a sensing module in a first IMD when a second IMD is present. For example, if RA pacemaker 12 was initially alone and RV pacemaker 14 is added to the system membership, programmer 50 may automatically program one or more sensing control parameters in RA pacemaker 12 and/or RV pacemaker 14. Altering sensing control parameters automatically in RA pacemaker 12 may enable sensing of far-field ventricular events by RA pacemaker 12. Automatic programming of certain sensing control parameters in RA pacemaker 12 based on the presence of RV pacemaker 14 may promote or avoid sensing of cardiac pacing pulses delivered by RV pacemaker 14 as needed according to an implemented sensing and therapy delivery algorithm which may coordinate pacing control between RA pacemaker 12 and RV pacemaker 14. A user may be unaware of changes in the automatically programmed sensing control parameters. In another example, programmer 50 may automatically program a tachyarrhythmia detection control parameter in ICD 30 based on identifying a pacemaker 12, 14 or 16 in the IMD system membership so that pacing pulses delivered by the pacemaker are appropriately handled by an implemented tachyarrhythmia detection algorithm, such as an ECG waveform analysis, in the ICD 30.

In another example, if both RA pacemaker 12 and at least one of RV pacemaker 14 and LV pacemaker 16 are present, programmer 50 establishes dual chamber pacing control parameters, which may include automatically programmed and/or user-programmable parameters that are display to and programmed by a user. Dual chamber pacing control parameters may include dual pacing mode selections such as DDI or DDD in addition to the single chamber pacing mode selections such as AAI or VVI.

When dual chamber pacing is selected, dual chamber pacing control parameters such as an atrioventricular (AV) interval are made available. Separately programmable paced AV delay and a sensed AV delay settings may be presented to a user when both RA pacemaker 12 and at least one of RV pacemaker 14 and LV pacemaker 16 are present as well as other programmable parameters that may relate to controlling dual chamber pacing, such as AV conduction monitoring control parameters and minimum ventricular pacing control parameters.

If LV pacemaker 16 is present, the programmer 50 may establish programmable parameters for controlling cardiac resynchronization therapy (CRT). CRT control parameters may include a programmable VV delay established by programmer 50 that is not displayed when only RA pacemaker 12 and/or RV pacemaker 14 are present without LV pacemaker 16.

The external control module 52 may provide user display 54 with established programmable parameter data at block 210 for generating a display, e.g., a graphical user interface, to a user for selecting and programming control parameters. The generated display may present programmable parameters for each individual IMD system member 12, 14, 16, 18 and/or 30 or present the programmable parameters for the IMD system 10 as a whole. For example, if RV pacemaker 14 or LV pacemaker 16 are available for delivering ATP when ICD 30 is present, a tachyarrhythmia therapy programming menu may be displayed that enables the user to program parameters for controlling ATP therapies, shock therapies, VT and VF detection and other tachyarrhythmia related functions of IMD system 10 without specifying to the user which IMD system member will receive a particular programming command. The user may select ATP therapy control parameters and shock therapy control parameters for programming from a tachyarrhythmia therapy programming menu. At block 212, programmer 50 transmits ATP therapy control parameters to the RV pacemaker 14 or LV pacemaker 16 that will be delivering the ATP and transmits the shock therapy control parameters to the ICD 30, without requiring the user to separately select programming menus for the individual IMD system members 14 or 16 and 30. In this way, the IMD system membership is programmed as a system by the user without requiring the user to individually program each IMD system member and contemplate how the individually programmed IMDs will interact with each other.

In response to a user-selected sensing or therapy control parameter, the programmer 50 generates and transmits the required programming commands sent to one or more of the IMD system members 12, 14, 16, 18 and/or 30 at block 212 to achieve the user-selected functionality. For example, in response to identifying RA pacemaker 12, at least one of RV pacemaker 14 or LV pacemaker 16, and ICD 30, programmer 50 may generate tachyarrhythmia therapy menu(s) for programming atrial tachyarrhythmia detection and therapies and programming ventricular tachyarrhythmia detection and therapies including ATP and shock therapies. The user may select and program the desired features without having to separately select the IMD system member(s) that will receive a programming command. In another example, programmer 50 may generate a display including a bradycardia therapy menu for programming dual chamber bradycardia pacing control parameters and/or CRT. The user may select and program desired control parameter settings for the IMD system as a whole without individually programming each of RA pacemaker 12, RV pacemaker 14 and LV pacemaker 16. In some cases a chamber-specific parameter, such as atrial sensing threshold, ventricular sensing threshold, atrial pacing pulse amplitude or ventricular pacing pulse amplitude, may be displayed on the bradycardia therapy menu, but the user does not need to view separate screens or displays for the specific RA pacemaker 12 or ventricular pacemaker 14 and/or 16 to select and program chamber-specific (and therefore device-specific) parameters.

Figure 6:
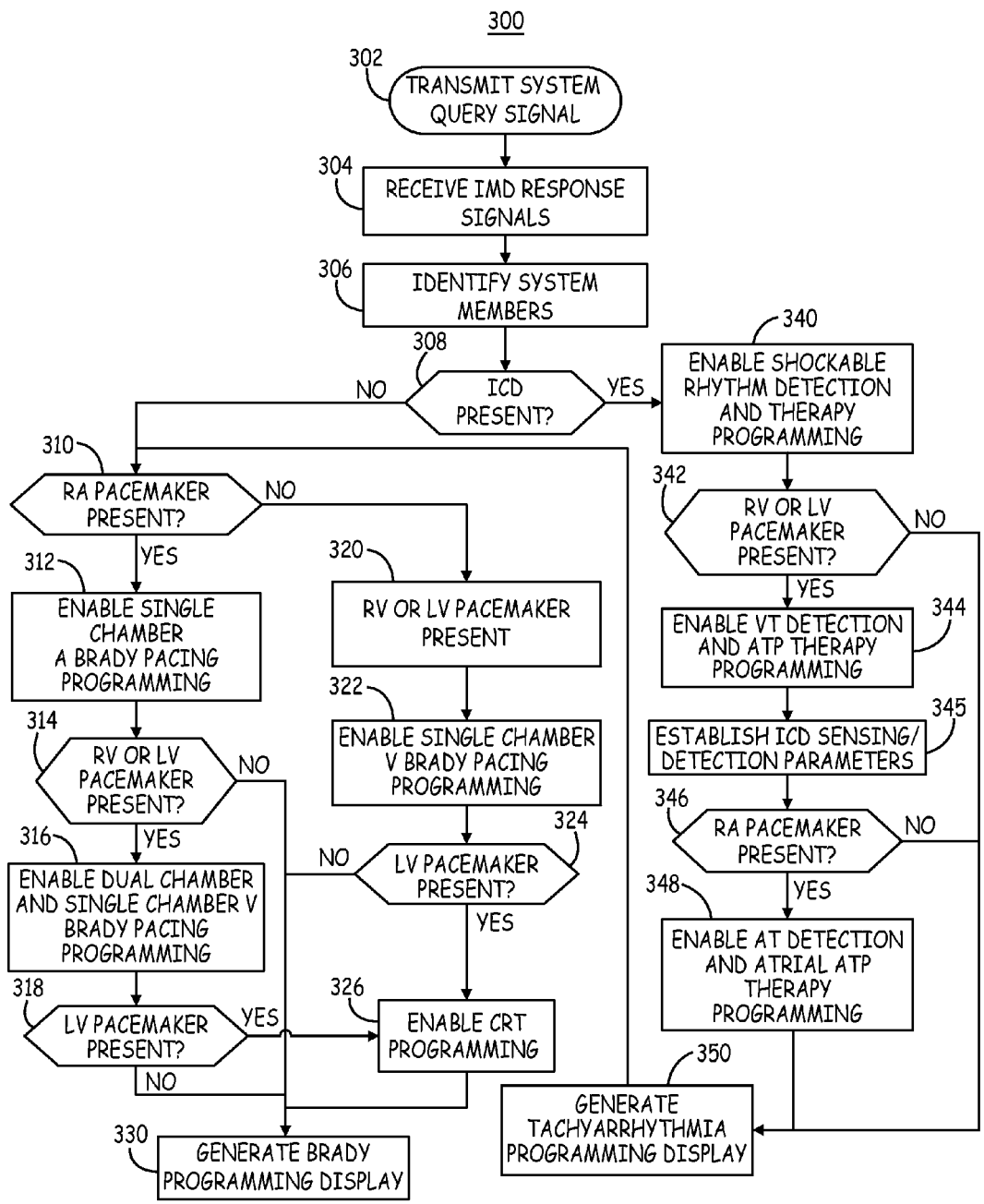
FIG. 6 is a flow chart of a method performed by an external programmer of an IMD system for establishing programmable parameters and generating programming displays to a user based on active members of an IMD system according to another example.

FIG. 6 is a flow chart 300 of a method performed by IMD system 10 for establishing programmable parameters and generating programming menus for display to a user according to another example. At block 302, programmer 50 transmits a system query signal. The IMD system members 12, 14, 16, 18 and/or 30 that are implanted in the patient respond to the query signal at block 304 so that the programmer 50 can identify the IMD system membership at block 306.

At block 308, programmer 50 determines if an ICD is present and active. If an ICD is present, e.g., ICD 30 shown in FIG. 1, shockable rhythm detection and shock therapy delivery programming is enabled at block 340. When enabled, the available programmable parameters and available settings for each parameter for controlling shockable rhythm detection by the ICD 30 and shock therapy delivery are established according to the ICD model identified by programmer 50.

At block 342, the programmer 50 determines if a ventricular pacemaker is present, such as RV pacemaker 14 or LV pacemaker 16 shown in FIG. 1. If at least one ventricular pacemaker is present, programming of VT detection and ventricular ATP therapies is enabled at block 344. The available programmable parameters and possible settings for each parameter for controlling VT detection and discrimination and controlling ATP therapies are established by programmer 50 according to the specific model of the ventricular pacemaker that is identified. In some cases, the possible ATP therapy parameters and settings may be dependent on the ICD model that is present in addition to the particular ventricular pacemaker model that is present.

If a ventricular pacemaker is present, ICD programmable sensing control parameters may be enabled at block 345 so that ICD 30 can be programmed to sense ventricular pacing pulses and/or use a tachyarrhythmia detection algorithm that is designed to handle the presence of ventricular pacing pulses. In some cases, a change to programmable sensing control parameters and/or tachyarrhythmia detection control parameters may be made automatically by programmer 50 without requiring user input. For example, external programmer 50 may enable ventricular pacing pulse sensing in ICD 30 automatically when a ventricular pacemaker 14 or 16 is determined to be present by adjusting a bandpass filter of the ICD sensing module, setting a pacing pulse sensing threshold, or making other sensing parameter adjustments. Sensed pacing pulse events may be identified to prevent inappropriate tachyarrhythmia detection.

If no ventricular pacemaker is present ("no" branch of block 342), or after enabling VT detection and ATP therapy programming at block 344, the programmer 50 determines if an atrial pacemaker is present, e.g., RA pacemaker 12 of FIG. 1, at block 346. If present, the programmer 50 enables atrial tachyarrhythmia (AT) detection and atrial ATP therapy programming at block 348. The particular programmable features and parameter values used for detecting AT and delivering atrial ATP therapy are established based in part on the atrial pacemaker model identified by programmer 50 and the other IMD system members.

Without a ventricular pacemaker present, such as RV pacemaker 14 or LV pacemaker 16, to provide the IMD system capability of delivering ventricular ATP, it may be undesirable to deliver atrial ATP. In some instances, ventricular tachycardia may occur in conjunction with AT or follow atrial ATP delivery. Accordingly, atrial ATP therapy may be disabled if a ventricular pacemaker is not present. In other examples, if RA pacemaker 12 is present but a ventricular pacemaker is not present, AT detection programming may be enabled at block 348 for monitoring purposes without enabling atrial ATP therapy programming.

If an atrial pacemaker is not present ("no" branch of block 346), AT detection and atrial ATP therapy programming is not enabled. In some IMD systems, a ventricular pacemaker or ICD may be configured to detect tachyarrhythmia and discriminate between supraventricular tachyarrhythmia arising in the atrial chambers of the patient's heart and ventricular tachyarrhythmia. As such, in some cases, even if an atrial pacemaker is not present such that AT detection and atrial ATP therapy programming is not enabled, programmable parameters used for SVT and VT discrimination may be enabled at block 340 and/or block 344 as part of the programmable features enabled when an ICD is present or when an ICD and ventricular pacemaker are both present.

After determining the IMD system membership that affects tachyarrhythmia detection and therapy delivery, the programmer control module 52 provides data to user display 54 for generating a tachyarrhythmia programming display to a user at block 350. The tachyarrhythmia programming display may include one or more menus displayed as screens or pages listing the various programmable parameters that can be selected by a user and the available parameter values or settings. The programmable parameters and available settings can then be selected from the tachyarrhythmia menu pages or screens by the user, e.g., using user interface 56 for selecting a desired value from a table, list, drop down menu or the like.

In the flow chart of 300, the process advances from block 350 after generating the tachyarrhythmia programming display to block 310 to evaluate which IMD system members are present that will influence the generation of a bradycardia programming display. It is recognized, however, that programmer 50 may simultaneously generate bradycardia programming display data and tachycardia programming display data based on the IMD system membership or that bradycardia programming display data is generated first then tachyarrhythmia programming display data is generated second.

At block 310, programmer 50 determines if an atrial pacemaker is present. In the flow chart 300 an atrial pacemaker is indicated as an RA pacemaker, e.g., RA pacemaker 12 shown in FIG. 1. In other examples, a left atrial pacemaker may be present in addition to or instead of RA pacemaker 12.

If an atrial pacemaker is present, single chamber atrial bradycardia pacing programming is enabled at block 312. The atrial bradycardia pacing parameters and available settings are established by programmer 50 based on the model of the atrial pacemaker identified. At block 314, programmer 50 determines if at least one ventricular pacemaker is present and, if so, enables dual chamber bradycardia pacing programming and single chamber ventricular pacing programming at block 316.

Programmable pacing modes and associated control parameters available when the atrial pacemaker is present without a ventricular pacemaker, programmable pacing modes and associated control parameter available when a ventricular pacemaker 14 or 16 is present without an atrial pacemaker 12, and pacing modes and associated control parameters available due to the presence of both atrial and ventricular pacemakers 12 and 14 or 16 are enabled and block 316. A user may select a single chamber atrial pacing mode (e.g., AAI, AAIR, or OAO modes), a single chamber ventricular pacing mode (e.g., VVI, VVIR, or OVO modes), or a dual chamber pacing mode (e.g., DDD or DDDR modes). Programmer 50 may establish DDDR as a user-programmable pacing mode at the system level without requiring the user to program the individual pacing modes of the RA pacemaker 12 and the RV pacemaker 14. A user-entered DDDR pacing mode may result in an automatically programmed VDD pacing mode in RV or LV pacemaker 14 or 16 and an automatically programmed ADDR pacing mode in RA pacemaker 12 to achieve the user-programmed DDDR pacing mode.

Programmer 50 may enable programming of a pacing mode in a given intracardiac pacemaker 12, 14 or 16 that wouldn't exist when the pacemaker 12, 14 or 16 is implanted without another pacemaker. For example, programmer 50 may establish a MVP option of DDDR pacing in which the IMD system pacing mode of the combined pacemakers 12 and 14 switches between AAIR (when AV conduction is intact) and DDDR (when AV conduction is not intact). The programmer 50 may automatically generate an ADIR pacing mode command to the RA pacemaker 12 in response to a user selecting the DDDR mode with MVP. The ADIR pacing mode may additionally be established and displayed as a programmable pacing mode for the overall IMD system 10. The ADIR pacing mode, whether programmed automatically by programmer 50 in response to a user-entered DDDR+MVP mode or added as a user-selectable pacing mode, may not be available when RA pacemaker 12 is implanted alone and may only be established by programmer 50 when a ventricular pacemaker 14 or 16 is present.

Based on the pacing mode selected, the programmer will generate the necessary commands to be transmitted to the IMD system 10. For example, if AAI is selected and a ventricular pacemaker 14 or 16 is implanted, the programmer 50 may generate an AAI pacing mode command transmitted to RA pacemaker 12 and an OVO pacing mode command to RV pacemaker 14 to achieve a system pacing mode of AAI. As described above, if a DDDR pacing mode is selected by the user, the programmer may automatically generate an ADDR pacing mode command transmitted to RA pacemaker 12 and a VDD pacing mode to the RV pacemaker 14. In this example, RA pacemaker 12 may be configured to sense far-field ventricular events, e.g., R-waves to achieve dual chamber sensing in the ADDR mode, and RV pacemaker 14 may be configured to sense far-field atrial events, e.g., P-waves, to achieve dual chamber sensing in the VDD mode.

At block 318, the programmer 50 determines if an LV pacemaker is present. Generally, an LV pacemaker, such as LV pacemaker 16, is implanted to provide CRT in a patient experiencing ventricular asynchrony. As such, if an LV pacemaker is present, programmer 50 enables CRT programming at block 326, which may include establishing a VV pacing interval.

If neither an ICD ("no" branch of block 308) nor an atrial pacemaker is present ("no" branch of block 310), at least one of RV pacemaker 14 and LV pacemaker 16 is present in the IMD system 10 in this example (assuming the patient has at least one therapy delivery device implanted). Programmer 50 enables single chamber ventricular bradycardia pacing programming at block 322. If an LV pacemaker is present, as determined at block 324, CRT programming may be enabled at block 326.

After determining which bradycardia pacing IMDs are present and active in the implanted system and enabling programming features according to the heart chambers in which pacing capabilities exist, programmer control module 52 provides user display 54 with the bradycardia programming data for generating a bradycardia programming display to a user at block 350. The bradycardia programming data may include sensing control parameters in the heart chambers in which pacing therapy is available as well as single, dual and multi-chamber pacing control parameters and/or CRT control parameters as needed. The bradycardia programming display may include one or more menus displayed as screens or pages listing the various programmable parameters that can be selected by a user and the available parameter values or settings. The programmable parameters and available settings can then be selected from the bradycardia menu pages or screens by the user, e.g., using user interface 56 for selecting a desired value from a table, list, drop down menu or the like.

In the example provided by flow chart 300, if an ICD is not present ("no" branch of block 308), tachyarrhythmia programming will be not be made available. In other examples, some limited features relating to detecting tachyarrhythmia, e.g., detecting and tracking atrial tachyarrhythmia burden by RA pacemaker 12 (if present) or detecting and storing VT episodes by ECG monitor 18 (if present), may be made available. Without an ICD present however, shock therapies are unavailable, and ATP therapies may be unavailable when the capability of back-up shock delivery is unavailable. Cardiac rhythm monitoring features may be included in a bradycardia programming display or in a separate rhythm monitoring programming display.

Figure 7:
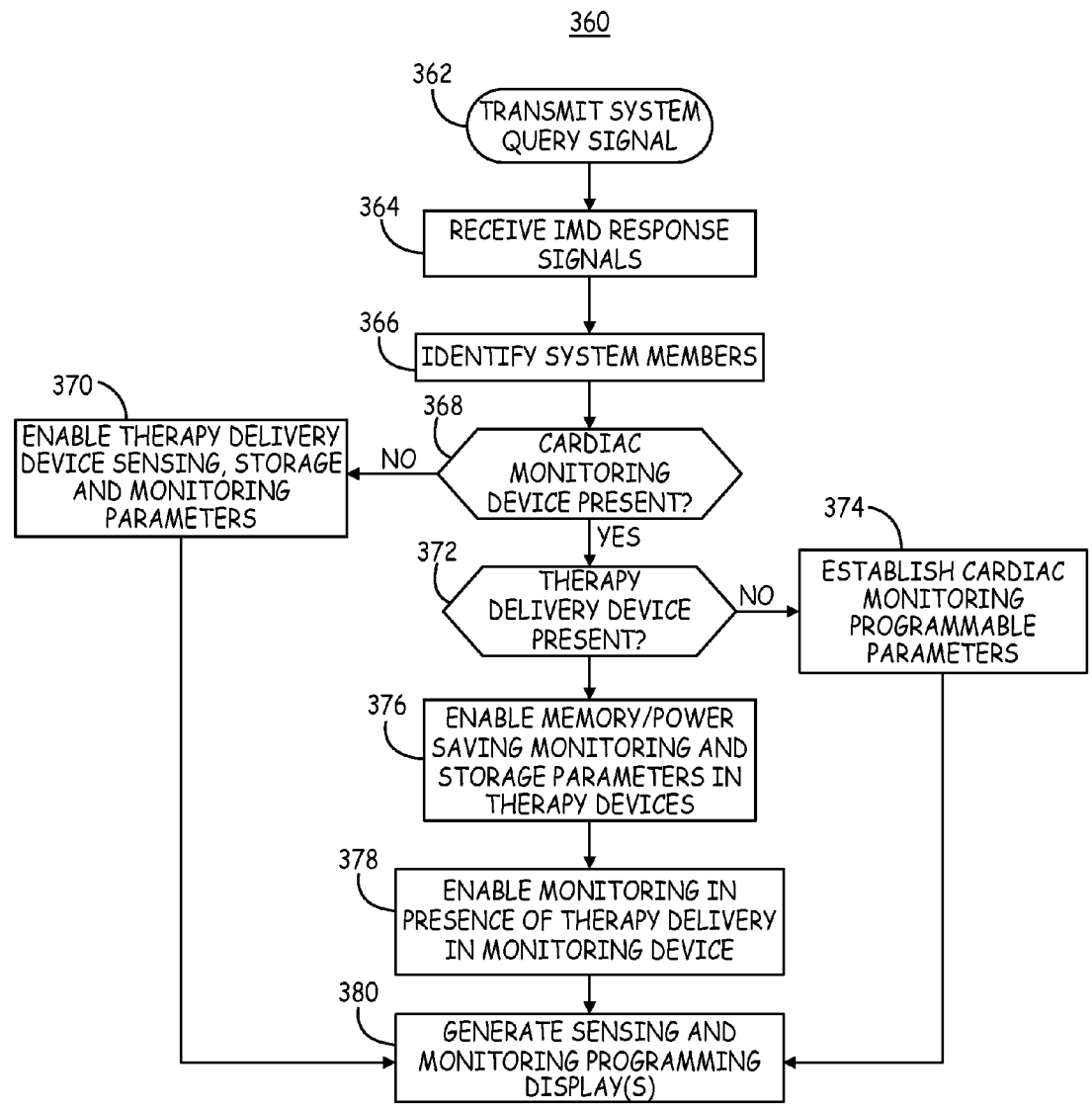
FIG. 7 is a flow chart of a method performed by the IMD system of FIG. 1 for establishing programmable parameters and generating a display of user-programming menus when a cardiac monitoring device is present in the patient.

FIG. 7 is a flow chart 360 of a method performed by IMD system 10 for establishing programmable parameters and generating a display of user-programming menus when a cardiac monitoring device 18 is present in the active IMD system membership. At block 362, programmer 50 transmits a system query signal. The IMD system members 12, 14, 16, 18 and/or 30 that are implanted in the patient respond to the query signal at block 364 so that programmer 50 can identify the system members at block 366.

At block 368, programmer 50 determines if a cardiac monitoring device, such as device 18, is an active IMD system member. The cardiac monitoring device 18 may be an ECG loop recorder capable of detecting arrhythmias and storing episodes of cardiac signal data in one example. If a cardiac monitoring device 18 is not identified at block 366, the programmer 50 establishes programmable parameters and generates associated user displays for controlling physiological signal sensing, storage and monitoring by therapy delivery devices 12, 14, 16 and/or 30 that have been identified as IMD system members at block 366. Monitoring and data storage functions may be enabled in a therapy delivery device, such as any of pacemakers 12, 14 or 16 and ICD 30, which are not enabled if cardiac monitoring device 30 is present.

For instance, if a pacemaker is present, such as RA pacemaker 12, RV pacemaker 14 or LV pacemaker 16, the pacemaker may be capable of detecting tachyarrhythmia and storing tachyarrhythmia episode data. If cardiac monitoring device 18 is not present, user-programmable parameters that control tachyarrhythmia detection by a pacemaker 12, 14, or 16 and storage of tachyarrhythmia episode data may be established and presented to the user by programmer 50. In other examples, tachyarrhythmia detection and episode storage may be enabled by an automatic programming command established and transmitted by programmer 50 without user input when programmer 50 recognizes that neither a cardiac monitoring device 18 nor an ICD 30 is present. Other programming of the therapy delivery IMDs 12, 14, 16 and/or 30 may proceed as described above in conjunction with FIG. 6.

If a cardiac monitoring device 18 is present, as determined at block 368, the programmer 50 determines whether a therapy delivery device is also present in the IMD system membership at block 372. If not, programmer 50 establishes programmable parameters for the cardiac monitoring device 18 at block 374 based on the capabilities of the monitoring device 18.

If a therapy delivery IMD is present, such as any of pacemakers 12, 14, 16 or ICD 30, the programmer 50 may enable memory and/or power saving monitoring and storage parameters for one or more of the therapy delivery IMDs 12, 14, 16 or 30. Continuing with the example given above, programmable parameters for tachyarrhythmia detection and episode storage that may be enabled in a pacemaker 12, 14, or 16 when cardiac monitoring device 18 is not present may be disabled or adjusted to a power-savings mode when cardiac monitoring device 18 is present. Tachyarrhythmia detection parameters may be enabled for pacemakers 12, 14, and/or 16, but episode storage may be disabled or reduced at block 376. Reduced episode storage may be established by an automatic programming command generated and transmitted to a pacemaker 12, 14 or 16 by programmer 50 without user input. Alternatively, user-programmable episode storage control parameters may be established and displayed by programmer 50 for receiving user input settings for tachyarrhythmia episode storage in the pacemaker 12, 14, or 16 or ICD 30. Similarly, episode storage capacity in ICD 30 may be reduced when cardiac monitoring device 18 is present.

Episode storage capacity may be reduced by reducing the total possible number of tachyarrhythmia episodes to be stored, reducing the duration of each stored episode, reducing the resolution of a stored cardiac signal, and/or reducing the types of data stored for each episode. For example, storage of a digitized cardiac electrical signal may be disabled automatically by programmer 50 such that only marker channel data and RR intervals are stored for detected tachyarrhythmia episodes by one of pacemakers 14 and 16. Programmer 50 may combine ECG signal data stored by cardiac monitoring device 18 with marker channel and interval measurements stored by a pacemaker 14 or 16 for display to a user for a given tachyarrhythmia episode.

At block 378, programmable parameters for controlling sensing of cardiac signals by the cardiac monitoring device 18 in the presence of cardiac electrical stimulation therapy delivery is enabled by programmer 50. Some cardiac signal sensing and tachyarrhythmia detection control parameters used by the cardiac monitoring device 18 may be modified when a therapy delivery device is present to avoid sensing pacing pulses as intrinsic cardiac events or counting a pacing pulse and subsequent evoked response as two different events. For example, blanking periods following sensed events and ECG signal filtering parameters may be automatically programmed to different settings in monitoring device 18 by programmer 50 when a pacemaker 12, 14 or 16 or ICD 30 is identified.

Monitoring algorithms used to detect arrhythmias, such as atrial fibrillation (AF) or ventricular tachyarrhythmia, may be modified when pacing pulses may be present. The programmer 50 may automatically switch to a monitoring algorithm for detecting AF that deals with the presence of pacing pulses from a monitoring algorithm used to detect AF when no pacemaker 12, 14 or 16 is present. In another example, AF monitoring by cardiac monitoring device 18 may be disabled if RA pacemaker 12 is present and enabled for AF monitoring or vice versa.

Cardiac event sensing control parameters may be established and programmed automatically by programmer 50 based on identifying an IMD system member as a therapy delivery device. Alternatively or additionally, user-programmable cardiac event sensing control parameters may be established and displayed by programmer 50 based on the presence of a therapy delivery device for programming cardiac monitoring device 18 for sensing in the presence of pacing pulses, cardioversion shock pulses or other cardiac electrical stimulation therapies.

At block 380, a display of sensing and monitoring programming menus is generated by programmer 50 based on the programming parameters enabled at blocks 370, 374 or 376 and 378. The programming displays may be presented at a system level in which programmable parameters relating to arrhythmia episode storage or other monitoring functions are displayed for the IMD system members as a whole without device-specific programming screens. Alternatively, programming parameters may be presented in a device-specific manner.

Figure 8:
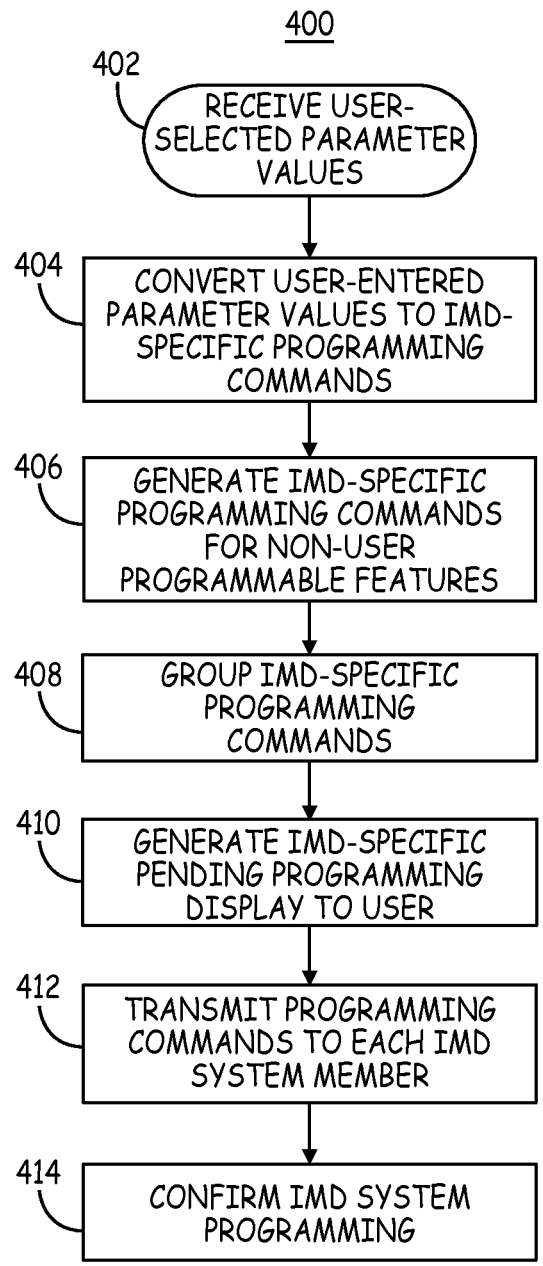
FIG. 8 is a flow chart of a method for programming IMD system members after establishing the programmable features of the IMD system.

FIG. 8 is a flow chart of a method for programming IMD system members 12, 14, 16, 18 and/or 30 after establishing the programmable features of the IMD system 10. As described above in conjunction with FIG. 6, a bradycardia programming display and/or a tachyarrhythmia programming display is/are generated by programmer 50 based on the IMD system membership. If a cardiac monitoring device 18 is present, a cardiac monitoring programming display may be generated as described in conjunction with FIG. 7. The programmer 50 receives any user-entered programmable parameter values selected by the user via the user interface 56.

At block 404, the programmer control module 52 converts the user-entered parameter values to IMD-specific programming commands. As described above, a bradycardia programming display may enable a user to select from among the available programmable parameter values to control single chamber pacing modes, dual chamber pacing modes, CRT, and/or other bradycardia therapy features as made available by programmer 50 based on IMD system membership. The programmer 50 converts parameters selected at a system level by the user interacting with the bradycardia programming display to the separate programming commands that are to be sent to the specific IMD members 12, 14, 16, 18 and/or 30 in order to achieve the user-selected system functionality. A single user-selected programmable parameter value may result in two or more distinct IMD-specific commands that will be transmitted to two or more different IMD system members 12, 14, 16, 18 and/or 30.

For example, if dual chamber pacing is selected by a user, the programmer 50 may automatically convert a user-entered DDDR pacing mode selection to an ADDR pacing mode command to be transmitted to RA pacemaker 12 and a VDD pacing mode command to be transmitted to the RV pacemaker 14. If the user selects dual chamber pacing with minimum ventricular pacing (MVP), the RA pacemaker 12 will receive an ADI pacing mode command and the RV pacemaker 14 will receive an OVO-VDD pacing mode command and an AV conduction monitoring command that enable the RV pacemaker 14 to switch between OVO and VDD pacing modes as needed depending on the status of AV conduction. The ADI pacing mode command is established and made available by the programmer 50 due to the presence of the RV pacemaker 14 and may be unavailable when RV pacemaker 14 (or LV pacemaker 16) is not present.

At block 406, the programmer control module 52 may generate IMD-specific programming commands to program IMD system features that are not user-programmable. For example, the programmer 50 may establish that an ICD 30 is not present and therefore ATP therapies should be turned OFF in RV pacemaker 14. The programmer 50 may automatically generate a programming command to be sent to RV pacemaker 14 to disable ATP to promote patient safety without requiring user input. In another example, if cardiac monitoring device 18 is present, storage of tachyarrhythmia episodes may be disabled in RA pacemaker 12, RV pacemaker 14 and LV pacemaker 16 to conserve memory and battery charge in the reduced-sized intracardiac pacemakers and eliminate or reduce redundant features between IMD system members.

If other devices are present that will likely be delivering pacing or shock pulses or other types of electrical stimulation pulses, therapeutic or diagnostic, parameters and/or algorithms that control sensing of cardiac events and detection of cardiac rhythms in the presence of cardiac electrical stimulation pulses from other devices may be automatically set by programmer 50. For example, sensing module filtering parameters, blanking intervals, or other sensing control parameters may be automatically programmed in one therapy delivery device, such as pacemakers 12, 14 or 16 or ICD 30, based on identifying another therapy delivery device in the IMD system membership which will be producing pacing pulses or shock pulses that may confound cardiac event sensing in another IMD.

Other programming commands may be automatically generated by programmer 50 to enable or disable other features to promote patient safety, minimize or eliminate functional redundancy, or avoid conflicting or unnecessary simultaneous therapy delivery from more than one device.

At block 408, IMD-specific programming command data are grouped by programmer 50 for transmission to the appropriate IMD system member 12, 14, 16, 18 or 30. For example, if the IMD system membership includes ICD 30 and RV pacemaker 14, a tachyarrhythmia programming display and a bradycardia programming display have been generated (as described in conjunction with FIG. 6). ATP therapies may be selected by a user from the tachyarrhythmia programming display. The programmer 50 may automatically convert user-entered VT detection control parameters and ATP therapy control parameters to programming commands to be transmitted to RV pacemaker 14. User-entered shockable rhythm detection and shock therapy control parameters are converted by programmer 50 to programmer commands to be transmitted to ICD 30. If the user has also selected single chamber ventricular pacing control parameters from the bradycardia programming display, the programmer 50 may convert the user-entered parameters to programming commands to be sent to RV pacemaker 14. At bock 408, the programmer 50 may group the programming command data relating to VT detection, ATP therapy delivery, and single-chamber ventricular pacing that are specific to RV pacemaker function into a telemetry transmission package to be transmitted to RV pacemaker 14 with appropriate RV pacemaker identification data. Programmer 50 also groups programming command data relating to shockable rhythm detection and shock therapy delivery in a telemetry transmission package to be transmitted to ICD 30 with appropriate ICD identification data. For example, each telemetry transmission package may include heading data that identifies the target IMD system member 14 or 30 so that the IMD system member can confirm proper receipt of the transmission package.

At block 410, prior to transmitting IMD-specific programming commands, programmer 50 may optionally generate IMD-specific programming summary report(s) for display to a user. The programming summary report may list the pending programmable feature values as converted by the programmer 50 to IMD-specific programming commands from the user-entered selection. Explanatory notations may be provided as to which pending values correspond to a user-entered selection. For example, an RA pacemaker pacing mode and an RV pacemaker pacing mode that have each been generated separately by programmer 50 based on a user-entered dual chamber pacing mode may be indicated in separate pending programming displays for each respective RA pacemaker 12 and RV pacemaker 14.

The separate pending programming values may be displayed with a notation that indicates the pending value is based on the user-selected dual chamber pacing mode. For example, if the RA pacemaker pending values include an ADDR pacing mode, and the user has selected a DDDR pacing mode, a notation may be included that indicates that this RA pacemaker pacing mode combined with a pending RV pacemaker VDD pacing mode will provide the user-selected DDDR pacing mode. The display of the IMD-specific pending values at block 410 is optional, but may be made available to a user so that the user can verify that the IMD system level programmable parameter values do not result in an unintended change in the functionality of an individual IMD system member.

In response to a user selecting a "program" button or accepting the pending programmable parameter values, the programmer 50 transmits the grouped programming command data to each IMD system member at block 412. The programmer 50 may transmit all programming data grouped into IMD-specific transmission packages simultaneously when the external telemetry module 58 is in an active communication session with all IMD system members simultaneously. Alternatively, programmer 50 may transmit grouped programming data sequentially in IMD-specific transmission packages sent one at a time to each of the IMD system members. Sequential programming may occur if a user is reviewing and accepting IMD-specific programming commands displayed at block 410 one at a time.

In some examples, a hierarchy of programming command transmission order may be established by programmer 50 to promote patient safety and expected IMD system 10 performance. It may be desirable to enable a function in one IMD system member prior to enabling a related or different function in another IMD system member. In other cases, it may be desirable to enable functions in different IMD system members substantially simultaneously. For example, it may be desirable to simultaneously program dual chamber pacing control parameters in RA pacemaker 12 and RV pacemaker 14 while it may be desirable to sequentially enable and program ICD shock therapy control parameters prior to enabling and programming RV pacemaker ATP therapies. As such, more than one grouping of IMD-specific programming commands may be produced by programmer 50 at block 408 to sequentially deliver IMD-specific programming commands and thereby enable IMD system features in a safe and logical manner.

After transmitting the programming commands to each IMD system member 12, 14, 16, 18 and/or 30 as needed at block 412, programmer 50 may be configured to receive a successful data transmission receipt from each IMD system member (or a "master" IMD system member). At block 414, programmer 50 may display a confirmation notice to the user to indicate successful programming of all IMD system members.

Figure 9:
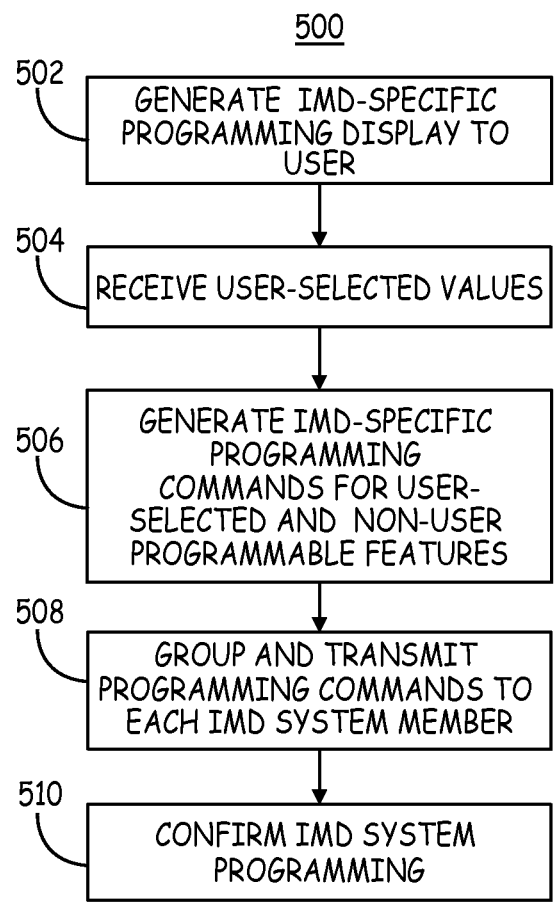
FIG. 9 is a flow chart of another method for programming implanted IMD system members by an external programmer.

FIG. 9 is a flow chart 500 of another method for programming IMD system 10 by programmer 50. In this example, the programmer 50 may generate bradycardia and tachyarrhythmia programming displays at block 502 that are IMD-specific displays so that the user may select programmable parameter values for each IMD system member one at a time. The programming displays include programmable features that are available in each IMD member 12, 14, 16, 18 and/or 30 based on the overall IMD system membership identified by programmer 50 and corresponding programmable parameters established by programmer 50 based on that membership.

After separately receiving the user-selected values for each IMD member, at block 504, e.g., via user interface 56, the programmer 50 generates IMD-specific programming commands at block 506, which may include programming commands generated in response to user input and non-user programmable programming commands generated automatically by the programmer 50 as needed.

The generated programming commands may be grouped into IMD-specific transmission packages as described above and transmitted to each IMD system member, simultaneously or sequentially, at block 508. At block 510, each IMD system member may transmit a confirmation receipt to programmer 50. Programmer 50 confirms the IMD system programming at block 510 by displaying an indication to the user that programming was successful based on programming confirmation receipts received from each IMD system member (either directly or via a "master" IMD system member).

FIG. 10 is a conceptual diagram of a look up table (LUT) 600 that may be stored in memory of programmer 50 for use by external control module 52, shown in FIG. 1, for establishing IMD system programmable parameters. The look-up table 600 may include a matrix of identified system membership 602 and associated programmable features 604 that are enabled or disabled. Programmer 50 provides to user display 54 the various user-programmable parameters and available settings that are needed to program the features 604 that are enabled based on IMD system membership 602. User display 54 generates a display of the corresponding programming menus, including the user-programmable parameters and available settings for the enabled features. In some instances, external control module 52 may generate programming commands to automatically enable a feature 604 that is to be enabled based on IMD system membership without requiring user input. Programmer 50 may also generate automatic programming commands to disable programmable features 604 that are not enabled or available based on IMD system membership. The programmable features 604 that are disabled based on IMD system membership may be excluded from the programming menus generated by the user display 54.

The examples of programmable features 604 listed in LUT 600 as being enabled or disabled based on IMD system membership 602 is intended to be illustrative in nature with no limitations intended. The list of programmable features 604 for each IMD system membership 602 is not intended to be an exhaustive list for the particular IMD system membership, and the combinations of enabled and disabled features based on IMD system membership may be different than the listed examples in LUT 600 in various embodiments.

It is to be understood, however, that in some examples the programmable parameters that are provided to enable a feature based on IMD system membership including two IMDs may be more than a mere combination of the features that are enabled for the two IMDs when they are implanted alone. For example, a programmable parameter that is established for a feature enabled when the IMD system membership includes RA pacemaker 12 and RV pacemaker 14 may not be established when RA pacemaker 12 is implanted without RV pacemaker 14 or when RV pacemaker 14 is implanted without RA pacemaker 12. In other words, the "whole may be more than a sum of its parts" in that the established programmable parameters for a combination of IMDs may be more than a sum of the established programmable parameters for each of the same IMDs individually.

Thus, a programmer and various methods for establishing programmable parameters and programming an IMD system including multiple IMDs in a given patient have been described according to illustrative embodiments. It is to be understood that numerous types of IMDs may be present in an IMD system and numerous variations of the functionality that may be achieved by a multi-device system may be conceived. The various methods disclosed herein may be implemented in different combinations than the illustrative examples described herein. One of ordinary skill in the art will appreciate that various modifications may be made to the described embodiments without departing from the scope of the following claims.

The invention claimed is:

1. An external medical device, comprising:
a telemetry module configured for bidirectional wireless communication with a plurality of implantable medical devices; and
a control module configured to:
determine an active membership of an implantable medical device (IMD) system, wherein the active membership comprises each one of the plurality of implantable medical devices that is present in a patient and operable,
establish programmable parameters for the IMD system based on the active membership, wherein the programmable parameters control at least one of a therapy delivery operation and a physiological signal sensing operation by each of the plurality of implantable medical devices of the active membership; and
control the telemetry module to transmit values for the established programmable parameters to the active membership.

2. The device of claim 1, further comprising:
a user display coupled to the control module; and
a user interface coupled to the control module,
wherein the control module is further configured to:
provide data to the user display for generating a programming display comprising user selectable values for at least a portion of the established programmable parameters;
receive a user-selected value via the user interface for at least one of the established programmable parameters; and
control the telemetry module to transmit the user-selected value to the active membership.

3. The device of claim 1, wherein the control module is further configured to:
- automatically generate a value for at least one of the established programmable parameters; and
- control the telemetry module to transmit the automatically generated value to the active membership.

4. The device of claim 3, wherein the control module is configured to automatically generate the value for at least one of the established programmable parameters by generating a sensing control parameter value for a first IMD of the active membership in response to identifying a second IMD of the active membership as a therapy delivery device.

5. The device of claim 1, further comprising:
- a user display coupled to the control module; and
- a user interface coupled to the control module,
- wherein the control module is further configured to:
  - determine a first active membership in response to identifying a first combination of the plurality of implantable medical devices present in the patient,
  - determine a second active membership in response to identifying a second combination of the plurality of implantable medical devices present in the patient, the second combination being different than the first combination;
  - establish a first set of programmable parameters when the first active membership is determined;
  - establish a second set of programmable parameters when the second active membership is determined; and
  - provide one of the first set of programmable parameters and the second set of programmable parameters to the user display for generating a respective one of a first programming display and a second programming display based on which one of the first active membership and the second active membership is determined.

6. The device of claim 5, wherein the control module is configured to:
- determine the first active membership by identifying a first IMD of the plurality of implantable medical devices;
- determine the second active membership by identifying the first IMD and a second IMD, the second IMD not present in the first active membership,
- wherein establishing the first set of programmable parameters comprises enabling a first programmable parameter for the first IMD and disabling a second programmable parameter for the first IMD based on the second IMD not being present in the first active membership; and
- wherein establishing the second set of programmable parameters comprises enabling both of the first programmable parameter for the first IMD and the second programmable parameter for the first IMD based on the second IMD being present in the second active membership.

7. The device of claim 6, wherein the user display is configured to generate the programming display by:
- generating a programming menu comprising the first programmable parameter for programming the first IMD when the first active membership is determined; and
- generating the programming menu comprising the first programmable parameter for programming the first IMD and the second programmable parameter for programming the first IMD when the second active membership is determined.

8. The device of claim 7, wherein the user display is configured to generate the programming menu as a bradycardia therapy programming menu.

9. The device of claim 7, wherein the control module is further configured to:
- provide the second set of programmable parameters comprising a multiple chamber pacing mode;
- convert the multiple chamber pacing mode parameter to a first programming command and second programming command in response to a user selecting the multiple chamber pacing mode parameter via the user interface;
- transmit the first programming command to the first IMD of the second active membership; and
- transmit the second programming command to the second IMD of the second active membership.

10. The device of claim 6, wherein the user display is configured to:
- generate the first programming display of a first programming menu comprising the first set of programmable parameters when the first active membership is determined; and
- generate the second programming display of the first programming menu and a second programming menu when the second active membership is determined, the second programming menu comprising the second set of programmable parameters,
- wherein the first set of programmable parameters control a first therapy delivered by the first IMD and the second set of programmable parameters control a second therapy delivered by the first IMD, the second therapy different than the first therapy.

11. The device of claim 10, wherein the user display is configured to generate the first programming menu as a bradycardia therapy menu comprising bradycardia pacing control parameters and generate the second programming menu as a tachyarrhythmia therapy menu comprising anti-tachycardia pacing therapy control parameters.

12. The device of claim 11, wherein the control module is further configured to:
- convert an anti-tachycardia pacing control parameter selected by a user from the second programming menu via the user interface to a first programming command;
- convert a shock therapy control parameter selected by a user from the second programming menu via the user interface to a second programming command;
- transmit the first programming command to the first IMD of the second active membership; and
- transmit the second programming command to the second IMD of the second active membership.

13. The device of claim 1, further comprising:
- a user display coupled to the control module;
- a user interface coupled to the control module;
- wherein the control module is further configured to:
  - provide data to the user display to generate a programming display comprising a user-selectable IMD system therapy control parameter;
  - responsive to a user selecting the IMD system therapy control parameter via the user interface, convert the IMD system therapy control parameter to a first programming command and a second programming command; and
  - control the telemetry module to transmit the first programming command to a first IMD of the active membership and transmit the second programming command to a second IMD of the active membership.

14. The device of claim 1, further comprising a memory storing a look-up table of programmable parameters for each of a plurality of different combinations of the plurality of implantable medical devices, the control module configured to establish the programmable parameters by acquiring the programmable parameters from the look-up table based on the determined active membership.

15. The device of claim 1, further comprising a user display, wherein the control module is further configured to:

merge data for a tachyarrhythmia episode received from different ones of the plurality of IMDs of the active membership; and provide the merged data to the user display for generating a single display of the tachyarrhythmia episode.

16. A method, comprising:

determining an active membership of an implantable medical device (IMD) system by a control module of an external medical device that is configured for bidirectional communication with a plurality of implantable medical devices, wherein the active membership comprises each one of the plurality of implantable medical devices that is present in a patient and operable, establishing programmable parameters for the IMD system based on the active membership, wherein the programmable parameters control at least one of a therapy delivery operation and a physiological signal sensing operation by each of the plurality of implantable medical devices of the active membership; and transmitting values for the established programmable parameters to the active membership.

17. The method of claim 16, further comprising:

providing data to a user display for generating a programming display comprising user selectable values for at least a portion of the established programmable parameters;

receiving a user-selected value via a user interface for at least one of the established programmable parameters; and transmitting the user-selected value to the active membership.

18. The method of claim 16, further comprising:

automatically generating a value for at least one of the established programmable parameters; and transmitting the automatically generated value to the active membership.

19. The method of claim 18, further comprising automatically generating the value for at least one of the established programmable parameters by generating a sensing control parameter value for a first IMD of the active membership in response to identifying a second IMD of the active membership as a therapy delivery device.

20. The method of claim 16, further comprising:

determining a first active membership in response to identifying by the control module a first combination of the plurality of implantable medical devices present in the patient determining a second active membership in response to identifying by the control module a second combination of the plurality of implantable medical devices present in the patient, the second combination being different than the first combination;

establishing a first set of programmable parameters when the first active membership is determined;

establishing a second set of programmable parameters when the second active membership is determined; and providing one of the first set of programmable parameters and the second set of programmable parameters to the user display for generating a respective one of a first programming display and a second programming display based on which one of the first active membership and the second active membership is determined.

21. The method of claim 20, further comprising determining the first active membership by identifying a first IMD of the plurality of implantable medical devices;

determining the second active membership by identifying the first IMD and a second IMD, the second IMD not present in the first active membership, establishing the first set of programmable parameters by enabling a first programmable parameter for the first IMD and disabling a second programmable parameter for the first IMD based on the second IMD not being present in the first active membership, and establishing the second set of programmable parameters by enabling both of the first programmable parameter for the first IMD and the second programmable parameter for the first IMD based on the second IMD being present in the second active membership.

22. The method of claim 21, further comprising generating the programming display by:

generating a programming menu comprising the first programmable parameter for programming the first IMD when the first active membership is determined; and generating the programming menu comprising the first programmable parameter for programming the first IMD and the second programmable parameter for programming the first IMD when the second active membership is determined.

23. The method of claim 22, further comprising generating the programming menu as a bradycardia therapy programming menu.

24. The method of claim 22, further comprising:

providing the second set of programmable parameters comprising a multiple chamber pacing mode;

converting the multiple chamber pacing mode to a first programming command and second programming command in response to a user selecting the multiple chamber pacing mode via the user interface;

transmitting the first programming command to the first IMD of the second active membership; and transmitting the second programming command to the second IMD of the second active membership.

25. The method of claim 21, further comprising generating the first programming display of a first programming menu comprising the first set of programmable parameters when the first active membership is determined; and generating the second programming display of the first programming menu and a second programming menu when the second active membership is determined, the second programming menu comprising the second set of programmable parameters, wherein the first set of programmable parameters control a first therapy delivered by the first IMD and the second set of programmable parameters control a second therapy delivered by the first IMD, the second therapy different than the first therapy.

26. The method of claim 25, further comprising generating the first programming menu as a bradycardia therapy menu comprising bradycardia pacing control parameters and generate the second programming menu as a tachyarrhythmia therapy menu comprising anti-tachycardia pacing therapy control parameters.

27. The method of claim 26, further comprising
converting an anti-tachycardia pacing control parameter selected by a user from the second programming menu via the user interface to a first programming command;
converting a shock therapy control parameter selected by a user from the second programming menu via the user interface to a second programming command;
transmit the first programming command to the first IMD of the second active membership; and
transmit the second programming command to the second IMD of the second active membership.

28. The method of claim 16, further comprising:
providing data to a user display to generate a programming display comprising a user-selectable IMD system therapy control parameter;
responsive to a user selecting the IMD system therapy control parameter via a user interface, converting the IMD system therapy control parameter to a first programming command and a second programming command;
transmitting the first programming command to a first IMD of the active membership; and
transmitting the second programming command to a second IMD of the active membership.

29. The method of claim 16, further comprising
storing a look-up table of programmable parameters for each of a plurality of different combinations of the plurality of implantable medical devices in a memory of the external device; and
establishing the programmable parameters by acquiring the programmable parameters from the look-up table based on the determined active membership.

30. The method of claim 16, further comprising:
merging data for a tachyarrhythmia episode received from different ones of the plurality of IMDs of the active membership; and
providing the merged data to the user display for generating a single display of the tachyarrhythmia episode.

31. An implantable medical device (IMD) system, comprising:
a plurality of implantable medical devices; and
an external device comprising:
a telemetry module configured for bidirectional wireless communication with the plurality of implantable medical devices; and
a control module coupled to the telemetry module and configured to:
determine an active membership of an implantable medical device (IMD) system, wherein the active membership comprises each one of the plurality of implantable medical devices that is present in a patient and operable,
establish programmable parameters for the IMD system based on the active membership, wherein the programmable parameters control at least one of a therapy delivery operation and a physiological signal sensing operation by each of the plurality of implantable medical devices of the active membership; and
control the telemetry module to transmit values for the established programmable parameters to the active membership.

32. A non-transitory, computer-readable storage medium comprising a set of instructions that when executed cause a control module of an external device that is configured for bi-directional communication with a plurality of implantable medical devices to:
determine an active membership of an implantable medical device (IMD) system, wherein the active membership comprises each one of the plurality of implantable medical devices that is present in a patient and operable,
establish programmable parameters for the IMD system based on the active membership; and
control the telemetry module to transmit values for the established programmable parameters to the active membership.

33. The non-transitory, computer-readable storage medium of claim 32, wherein the programmable parameters control at least one of a therapy delivery operation and a physiological signal sensing operation by each of the plurality of implantable medical devices of the active membership.

* * * * *